US008623414B2

(12) United States Patent
Tonge

(10) Patent No.: US 8,623,414 B2
(45) Date of Patent: Jan. 7, 2014

(54) COMPOSITIONS COMPRISING A LIPID AND COPOLYMER OF STYRENE AND MALEIC ACID

(75) Inventor: Stephen Tonge, Worcester Worcestershire (GB)

(73) Assignee: Malvren Cosmeceutics Limited, Worchestershire (GB)

( * ) Notice: Subject to any disclaimer, the term of this patent is extended or adjusted under 35 U.S.C. 154(b) by 972 days.

(21) Appl. No.: 11/921,262

(22) PCT Filed: May 31, 2006

(86) PCT No.: PCT/GB2006/050134
§ 371 (c)(1),
(2), (4) Date: Nov. 29, 2007

(87) PCT Pub. No.: WO2006/129127
PCT Pub. Date: Dec. 7, 2006

(65) Prior Publication Data
US 2009/0155375 A1 Jun. 18, 2009

(30) Foreign Application Priority Data

May 31, 2005 (GB) .................................. 0510968.1

(51) Int. Cl.
*A61K 9/14* (2006.01)
*A61K 9/127* (2006.01)
*C08F 22/06* (2006.01)
*C08L 9/06* (2006.01)
*C08L 25/04* (2006.01)

(52) U.S. Cl.
CPC . *A61K 9/14* (2013.01); *A61K 9/127* (2013.01); *C08F 22/06* (2013.01); *C08L 9/06* (2013.01); *C08L 25/04* (2013.01); *Y10S 977/773* (2013.01); *Y10S 977/797* (2013.01); *Y10S 977/906* (2013.01); *Y10S 977/907* (2013.01)
USPC .......... 424/489; 424/450; 424/78.2; 424/501; 977/773; 977/797; 977/906; 977/907; 514/772.6; 977/773

(58) Field of Classification Search
None
See application file for complete search history.

(56) References Cited

U.S. PATENT DOCUMENTS

| 2,897,121 | A |   | 7/1958 | Wagner |
|-----------|---|---|--------|--------|
| 4,435,383 | A | * | 3/1984 | Wysong ........................ 424/408 |
| 4,732,933 | A | * | 3/1988 | Maeda et al. .............. 424/78.21 |
| 5,024,995 | A | * | 6/1991 | Robertson et al. ............... 514/21 |
| 5,430,021 | A | * | 7/1995 | Rudnic et al. .................... 514/14 |
| 6,436,905 | B1 | * | 8/2002 | Tonge et al. ...................... 514/23 |
| 6,531,160 | B2 |   | 3/2003 | Biatry et al. |
| 2002/0022038 | A1 | * | 2/2002 | Biatry et al. .................. 424/401 |
| 2004/0001792 | A1 |   | 1/2004 | Biatry |
| 2004/0042990 | A1 |   | 3/2004 | Biatry |
| 2004/0047824 | A1 |   | 3/2004 | Biatry |
| 2004/0052739 | A1 |   | 3/2004 | Biatry |
| 2004/0096406 | A1 |   | 5/2004 | De Poilly |
| 2004/0175342 | A1 |   | 9/2004 | Biatry |

FOREIGN PATENT DOCUMENTS

| EP | 0158441 | 10/1985 |
|----|---------|---------|
| JP | 64-061424 | 3/1989 |
| JP | 06 106047 | 4/1994 |
| JP | 06106047 | 4/1994 |
| WO | 95/11700 | 5/1995 |
| WO | 99/09955 | 3/1999 |
| WO | 00/37547 | 6/2000 |
| WO | 01/96012 | 12/2001 |

OTHER PUBLICATIONS

Sartomer Product Bulletin: SMA Multi-Functional Resins. Sep. 2004 (see last page for date). 15 pages.*
International Search Report (PCT/ISA/210).
Tonge S R et al: "Responsive hydrophobically associating polymers: A review of structure and properties", Advanced Drug Delivery Reviews, Amsterdam, NL, vol. 53, No. 1, (Dec. 3, 2001), pp. 109-122, XP002276152, ISSN: 0169:409X.
(Seki, K and Tirrell, D *Macromolecules* 1983 17:1692-1698; Tirrell, D, Takigawa, D and Seki, K *Ann. New York Acad. Sci.* 1985 446:237-248; Thomas, JL, Devlin BP and Tirrell, DA *Biochimica et Biophysica Acta* 1996 1278:73-78).
(Sugai, S and Ohno, N *Biophys. Chem.* 1980 11:387-395).
(Borden, KA, Voycheck, CL, Tan, IS and Tirrell DA *Polym. Prep. (Am. Chem. Soc. Div. Poly. Chem.)* 1987 28(1):284-285).
(Trivedi, BC and Culbertson, BM *Maleic Anhydride*, Plenum (1982), ISBN 0306409291).
(Fried, J *Polymer Science and Technology*, 2$^{nd}$ Ed, Prentice Hall (2003), ISBN 0130181684).
(Carney, LG and Hill, RM *Arch. Ophthalmol.* 1976 94(5):821-824).
(Cevc, G *Advanced Drug Delivery Reviews* 2004 56:675-711).
(Sanders, CR and Landis, GC *Biochemistry* 1995 34(12):4030-4040).
H. Maeda, SMANCS and . . . , Advanced Drug Delivery Review 46 (2001) 169-185 Chain-Growth Polymerization, p. 43.
P. Hwang, Solution Structure . . . , PNAS (Oct. 15, 2002) 00/99, No. 21, 13560-13565.

* cited by examiner

*Primary Examiner* — Frederick Krass
*Assistant Examiner* — Isaac Shomer
(74) *Attorney, Agent, or Firm* — Klauber & Jackson LLC

(57) ABSTRACT

A composition comprising a lipid and copolymer of styrene and maleic acid, wherein the copolymer of styrene and maleic acid is non-alternating, and wherein the polymer and lipid are in the form of macromolecular assemblies.

45 Claims, No Drawings

COMPOSITIONS COMPRISING A LIPID AND COPOLYMER OF STYRENE AND MALEIC ACID

The present application is based on, and claims priority from International Application Number PCT/GB2006/050134, filed May 31, 2006, and United Kingdom Application No. GB 0510968.1, filed May 31, 2005, the disclosure of which is hereby incorporated by reference herein in its entirety.

The present invention relates to compositions of use in the solubilisation of hydrophobic substances, particularly in the solubilisation of hydrophobic active agents which are of use in the field of cosmetics or pharmaceuticals, and in the solubilisation of peptides and proteins for the investigation of their structure and their interactions with other substances.

Poor water solubility presents a fundamental problem in delivering oil-soluble active materials to sites within or topically upon the body. Numerous formulating aids have been adopted to overcome this limitation, aiming to produce aqueous formulations that are more functionally and/or aesthetically acceptable. Approaches include the use of surfactant systems, liposomes, niosomes and cyclodextrins, amongst others. However, all of these systems have particular drawbacks. For example: liposomes and cyclodextrins may have a low loading capacity; liposomal formulations may be rapidly removed from the systemic circulation after intravenous administration; both liposomes and niosomes may suffer from a lack of clarity; and the use of certain surfactants may result in the formation of irritating compositions.

Oil soluble active materials are frequently applied to the skin as part of water-in-oil or oil-in-water emulsions, typically in the form of creams or lotions. These are generally oily to the touch and may be aesthetically unpleasant, leading to a low consumer appeal. Furthermore, they may be physically unstable, tending to separate out or "cream" on standing, limiting both the shelf-life and potentially causing heterogeneity in the composition which may lead to unpredictability in the application of active agents.

Hydrophobically associating polymers (also known as amphipols or hypercoiling polymers, due to their amphiphilic character) may associate with phospholipids to form flattened disk-like molecular assemblies. For example, homopolymers of ethacrylic acid (i.e. poly[2-ethacrylic acid], also known as PEAA) have been shown to interact with pure DLPC, DMPC, DPPC, DSPC (respectively di-lauryl, di-myristyl, di-palmityl and di-stearyl phosphatidyl choline) and DPPG (di-palmityl phosphatidyl glycerol), and also a mixture of DPPC/DPPA (di-palmityl phospatidic acid) resulting in the formation of optically clear, aqueous solutions (Seki, K and Tirrell, D Macromolecules 1983 17:1692-1698; Tirrell, D, Takigawa, D and Seki, K Ann. New York Acad. Sci. 1985 446:237-248; Thomas, J L, Devlin B P and Tirrell, D A Biochimica et Biophysica Acta 1996 1278:73-78). This effect is the result of a conformational transition from the extended chain typical of a polyelectrolyte, through an intermediate state as a random coil, to a compact hypercoiled state at low pH.

Other hydrophobically associating polymers are also known to interact with phospholipids to form macromolecular assemblies, such as copolymers which contain hydrophilic and hydrophobic monomer components. International Patent Application WO99/009955 (equivalent to granted patents EP1007002 and U.S. Pat. No. 6,426,905) discloses the use of hydrolysed alternating copolymers of maleic anhydride (anionic, hydrophilic in its hydrolysed maleic acid form) and either styrene or an alkyl vinyl ether (hydrophobic). Structures in the region of 10-40 nm in diameter were prepared using a hydrolysed alternating polymer of maleic anhydride and styrene, in conjunction with pure DLPC or DPPC (for further information see the review article—Tonge, S R and Tighe, B J Advanced Drug Delivery Reviews 2001 53:109-122).

Alternating Copolymers of Styrene and Maleic Anhydride

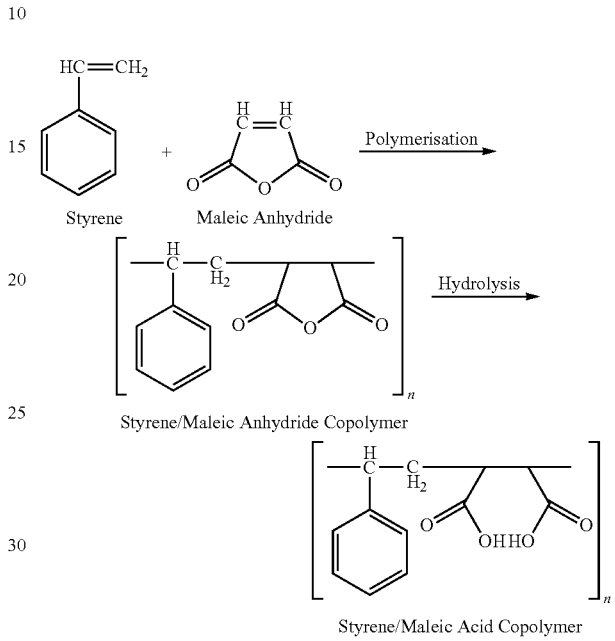

Such polymer/lipid macromolecular complexes have been proposed as a means for the solubilisation of active agents with poor aqueous solubility. However, both of these systems suffer from a number of disadvantages. PEAA is not commercially available and its suitability for use in cosmetics and pharmaceuticals has not yet been determined. Furthermore, these synthetic polymers only interact with phospholipids to form macromolecular assemblies at a pH level near or below their respective $pK_a$ value, in the case of PEAA this is 6.5 (Fichtner, F and Schonert, H Colloid & Polymer Sci. 1977 255:230-232; Thomas, J L, Devlin B P and Tirrell D A Biochimica et Biophysica Acta 1996 1278:73-78).

Alternating copolymers of styrene and maleic acid (i.e. hydrolysed styrene/maleic anhydride polymers) have a $pK_a$ value in the region of 3.75-4.0 (Sugai, S and Ohno, N Biophys. Chem. 1980 11:387-395), the $pK_a$ for the individual acid functions being approximately 1.97 and 6.24. Preparation of clear solutions, and hence macromolecular assemblies, requires a lowering of the pH to between 3-5. Such pH levels are not generally suitable for compositions which are to be applied to sensitive surfaces of the body. Although the pH of these alternating copolymer formulations may be raised after the formation of the polymer/lipid complex, such adjustment leads to instability, which may be observed as a loss of clarity over time as the macromolecular assemblies degrade.

Although styrene/maleic anhydride or the corresponding maleic acid hydrolysis product and half esters have been widely employed in industrial and household applications, including use as coatings, and for emulsification and dispersant purposes, these polymers have had limited application in personal care and biomedical products.

Copolymers of styrene and maleic anhydride have been described for use in cosmetics, as a means of stabilizing ascorbic acid and its hydrophilic derivatives, for the purpose of depigmenting skin, anti-aging, for protection from UV radiation, sunburn and in preventing loss of firmness and/or elasticity from the skin (as disclosed in US20040001792, US20040042990, US20040052739 and US20040047824) or for promoting the synthesis of epidermal ceramides and improving the barrier function of the skin to moisturise the skin and improve complexion (US20040175342) and for incorporating a metal salt of phosphorylated ascorbic acid for use in depigmenting the skin and as an anti-wrinkle and anti-aging agent (US20040096406). In each case, there is preferably used a 1:1 copolymer of maleic anhydride and styrene. The use of the polymer as a component in the formation of a water insoluble waxy coat of a microcapsule containing an aqueous core suitable for cosmetic or dermatological use is disclosed in U.S. Pat. No. 6,531,160.

The poly[styrene-co-maleic acid/anhydride]half butyl ester is described in U.S. Pat. No. 4,732,933 as a pharmaceutical preparation conjugated to the antitumor agent neocarcinostatin, where the polymer acts to raise both the molecular weight and lipophilicity, so leading to accumulation of the drug in certain target tissues. This polymer drug conjugate is known as SMANCS (Maeda, H *Advanced Drug Delivery Reviews* 2001 46:169-185). JP01061424A discloses a pharmaceutical formulation of SMANCS, a conjugate of a styrene/maleic acid monobutyl ester copolymer bound to molecules of the drug neocarcinostatin, prepared by mixing a solution of SMANCS in ammonium carbonate buffer (pH 7.5 to 9.5) with a solution of a phospholipid such as egg yolk also in ammonium carbonate buffer (pH 7.5 to 9.5) to form a mixture which after being freeze dried to remove water is dispersed in a non-aqueous oily contrast medium so as then to provide a clear and transparent dispersion therein of the SMANCS conjugate.

There is clearly a need to produce a stable, non-irritating formulating aid that enables oil-soluble active agents to be incorporated into an aqueous medium at high concentration, while at the same time forming macromolecular complexes that are small enough not to disrupt the passage of light through the resultant solution, i.e. to remain substantially clear.

It has surprisingly been found, contrary the expectations of one skilled in the art, and in contrast to the teaching of WO99/009955, that hydrolysed block copolymers of styrene/maleic anhydride (i.e. block copolymers of styrene/maleic acid) may be used in the preparation of polymer/lipid complexes, such polymer/lipid complexes being of use for example in the solubilisation of oil-soluble active agents. Compositions comprising hydrolysed block copolymers of styrene/maleic anhydride may have one or more of the following advantages compared to the approaches of the prior art:

(i) be more stable
(ii) result in less irritation
(iii) allow a higher loading of active agent
(iv) enable oil-soluble active agents to be formulated as substantially clear aqueous solutions
(v) facilitate enhanced penetration through the skin
(vi) enable membrane proteins and/or peptides to be solubilised in an environment which closely mimics native membranes In a first aspect of the present invention there is provided a composition comprising a lipid and copolymer of styrene and maleic acid, wherein the copolymer of styrene and maleic acid is non-alternating, and wherein the polymer and lipid are in the form of macromolecular assemblies. Such compositions may be referred to herein as compositions of the invention.

According to the present invention there is also provided a composition comprising a lipid and copolymer of styrene and maleic acid, wherein the ratio of styrene to maleic acid monomer units is greater than 1:1, wherein the polymer and lipid are in the form of macromolecular assemblies. Such compositions are examples of compositions of the invention.

Monomer ratios stated for polymers are defined on the basis of the number of each monomer unit in the polymer, for example, a ratio of styrene and maleic anhydride of 3:1 indicates that there are three styrene monomer units for each maleic anhydride monomer unit in the polymer chain. It will be understood that the stated monomer ratios are averages and, as a result of the uncertainty in polymerisation reactions, do not necessarily represent the exact ratio for any specific polymer chain. Typically greater than 50%, in particular greater than 75% and especially greater than 90% (on a weight to weight basis) and suitably all of the polymer chains will have a monomer ratio which is within 50%, such as within 35%, suitably 25% (for example within 15%), more particularly within 10% and especially within 5% of the stated value. For example, a ratio of styrene and maleic anhydride of 3:1 with 10% variation covers 3.3:1 to 2.7:1.

The presence of a macromolecular assembly (an association of individual molecules within a macromolecular structure which is not maintained by covalent bonding), also referred to as a macromolecular complex, may be confirmed by a number of means available to those skilled in the art for the determination of particle size, for example, electron microscopy (such as used in Tonge, S R and Tighe, B J *Advanced Drug Delivery Reviews* 2001 53:109-122 for macromolecular assemblies incorporating alternating styrene/maleic acid copolymers) or laser diffraction techniques. However, in practice the formation of macromolecular assemblies will often be visible to the naked eye. For example, when a cloudy emulsion of polymer and lipid is prepared at relatively high pH (such that the polymer is highly charged and most likely in the form of an extended chain), and the pH is then subsequently lowered to a level where the hydrophilic/hydrophobic balance in the polymer chain is suitable for the formation of macromolecular assemblies (this pH level may be referred to as the critical pH) a noticeable solubilisation of lipid may be seen to occur which, depending on the quantities and exact nature of the individual components present, results in a marked partial or complete clearing of the mixture.

The critical pH refers to the pH level below which macromolecular assemblies may form. Styrene/maleic acid copolymers have different critical pH values depending upon their specific monomer ratios, the greater the styrene content the higher the critical pH. Once formed, the pH of a solution containing macromolecular assemblies may be raised above the critical pH, although macromolecular assemblies are generally not stable under such conditions and will degrade over time (substantial increases over the critical pH typically result in a more rapid degradation). pH levels which are substantially below the critical pH may also cause the macromolecular assemblies to degrade, as the hydrophobicity of the polymer chains may reach a level where the polymer is no longer soluble in water.

The term "blocky", as used herein in relation to copolymers, refers to the fact that the monomer units within the polymer are distributed in a non-alternating manner. By definition, copolymers containing a monomer ratio other than 1:1 cannot be alternating due to the presence of blocks containing more than one unit of a single monomer. Copolymers having a monomer ratio of 1:1 may be alternating or may be blocky in nature, depending upon the monomers present and the process of manufacture.

The hydrolysed styrene/maleic anhydride copolymer of use in the present invention will be non-alternating, i.e. the styrene and maleic acid residues will not be arranged in an alternating relationship.

The clarity of a solution may be determined by methods known to those skilled in the art, for example, through the use of a turbidity meter, such as those provided by Orbeco-Helling. Other providers of turbidity measurement apparatus include Hach-Lange. Turbidity may be based on a number of standard units, such as nephelometric turbidity units (NTU). Nephelometric turbidity units (NTU) are directly interchangeable with formazin nephelometric units (FNU). By the term "clear", when used herein, is meant a solution with a turbidity reading of less than 150 NTU, especially less than 100 NTU, in particular less than 50 NTU, suitably less than 25 NTU (e.g. less than 5 NTU). Colourless solutions are those that transmit light without absorbance of any particular visible wavelength. Clear solutions may be coloured where they contain a component which absorbs light within the visible range (e.g. certain active agents, or colorants).

The terms "stable", and where appropriate "stability", when used herein in relation to the clarity of a solution, refer to the ability of a solution to remain at a constant clarity. Typically the clarity of a solution will remain substantially unchanged (for example, changing by less than 100 NTU, especially less than 50 NTU, in particular less than 25 NTU and suitably less than 5 NTU) over a period of time (for example, at least one day, especially at least one week, in particular at least one month and suitably at least six months) when stored at constant temperature (for example, at 4° C., suitably at 25° C.).

An alternative definition of "stable" (and where appropriate "stability") is where the clarity of a solution, although showing some degree of variation over a given time period, remains within a desired turbidity range. In this case, typically the solution will have a turbidity reading which remains less than 150 NTU, especially less than 100 NTU, in particular less than 50 NTU, suitably less than 25 NTU (e.g. less than 5 NTU) for a period of time (for example, at least one day, especially at least one week, in particular at least one month and suitably at least six months) when stored at constant temperature (for example, at 4° C., suitably at 25° C.).

In one embodiment of the invention a stable solution is one which remains substantially unchanged over a period of time (as described above). In a second embodiment of the invention a stable solution is one which remains within a desired turbidity range for a period of time (as described above). In a third embodiment of the invention a stable solution is one which remains substantially unchanged and within a desired turbidity range over a period of time (as described above).

As discussed previously, WO99/009955 teaches that in order to interact with membrane forming lipids to form macromolecular structures in the order of 10-40 nm in diameter (therefore smaller that the wavelength of light, appearing substantially clear and colourless in aqueous solution), the polymer must be in the form of an alternating copolymer (i.e. a non-block copolymer) having a linear backbone along which hydrophobic groups and anionic hydrophilic groups are evenly arranged.

One skilled in the art would anticipate that the precisely defined molecular architecture of a homopolymer or an alternating copolymer is required for the formation of an amphipathic coiled structure, and it is this structure which is believed to be required for interaction with lipid (Borden, K A, Voycheck, C L, Tan, I S and Tirrell D A *Polym. Prep. (Am. Chem. Soc. Div. Poly. Chem.)* 1987 28(1):284-285). Replacement of the homopolymer or alternating styrene/maleic acid copolymer with a blocky styrene/maleic acid copolymer would not be expected to demonstrate a similar interaction with membrane forming lipids. It has now surprisingly been found that it is not in fact necessary to use a homopolymer or copolymer with strict alternation of hydrophobic and hydrophilic monomer units, but that blocky copolymers of styrene and maleic anhydride in the hydrolysed form (i.e. as styrene/maleic acid) may also interact with lipids to form polymer/lipid macromolecular complexes, thereby forming substantially clear and colourless aqueous solutions.

Without being limited by theory, it is believed that although the $pK_a$ of the acid functions in a blocky polymer may be subtly different from that in an alternating polymer, the pH at which the lipid interaction occurs is mainly dependent upon the attainment of a particular hydrophilic/hydrophobic balance within the polymer chains. Alternating polymers of styrene and maleic acid, as a result of their relatively high acid content, require a significant proportion of the acid functions to be neutralised before the correct hydrophilic/hydrophobic balance is obtained, only initiating an interaction with lipids at a pH in the region of 3 to 5, and which interaction becomes unstable once the pH has been raised substantially above this level (for example above pH 5.5). Blocky copolymers of styrene and maleic acid wherein the ratio of styrene and maleic acid residues is greater than 1:1 are more hydrophobic due to the presence of a higher proportion of styrene monomer units and fewer maleic acid monomer units. As such, in order to obtain the correct hydrophilic/hydrophobic balance a smaller proportion of the acid functions must be neutralised (i.e. the balance may be obtained at a higher pH). In light of this finding, it is possible to tailor the ratio of the styrene and maleic anhydride monomer units such that the polymer interacts with lipid over a specific pH range, thereby enabling the selection of a styrene/maleic acid copolymer which is ideally suited for a chosen application.

Free-radical-initiated copolymerisation of styrene and maleic anhydride is an extremely well characterised polymerisation reaction (Trivedi, B C and Culbertson, B M *Maleic Anhydride*, Plenum (1982), ISBN 0306409291). The reactivity ratios, $r_1$ and $r_2$, for any monomer pair may be used as an index for evaluating the alternating frequency in copolymerisation reactions. Ideal (i.e. random) copolymerisation conditions exist when $r_1$, $r_2$ and $r_1 r_2$ are equal to 1. Where $r_1$, $r_2$ and $r_1 r_2$ tend to zero, the degree of alternation increases. The reactivity ratios $r_1$ and $r_2$ of styrene (monomer 1) with maleic anhydride (monomer 2) are 0.097 and 0.001 respectively (Fried, J *Polymer Science and Technology*, $2^{nd}$ Ed, Prentice Hall (2003), ISBN 0130181684), indicating that although both monomers preferentially react with the other, styrene is significantly less discriminating than maleic anhydride. Consequently, the sequence distribution within a copolymer of styrene and maleic anhydride depends upon the monomer feed composition and the resulting copolymers can differ from 1:1 alternation. In cases where the ratio of styrene to maleic anhydride is greater than 1:1 (for example 2:1, 3:1 or 4:1) an increasing number of styrene-styrene sequences are present.

Styrene/maleic anhydride copolymers are conveniently prepared by a precipitation process, typically in an aromatic hydrocarbon solvent, for example toluene or dichlorobenzene. Polymerisation may be initiated using free-radical initiators, for example AIBN (azoisobutyronitrile) and the molecular weight may be controlled by the use of end-capping agents such as highly alkylated aromatic hydrocarbons, for example p-cymene. The ratio of monomers in the polymer may be controlled by variation of the feed composition, and may be determined by means known to those skilled in the art, for example by titration to determine maleic acid content of the hydrolysed polymer.

Styrene/maleic acid copolymers of use in the present invention will typically have an average molecular weight ($M_w$) of less than 500,000 daltons, especially less than 150,000 daltons, in particular less than 50,000 daltons and suitably less than 20,000 daltons (for example 1,500 to 15,000 daltons). $M_w/M_n$ ($M_n$ being the number average molecular weight) indicates the polydispersity, and will typically be less than 5, especially less than 4, in particular less than 3 and suitably less than 2 (for example less than 1.5). Polymers should be of sufficient length such that they may demonstrate the ability to hypercoil, but are suitably not so long as to introduce difficulties with viscosity as a result of interchain interactions.

A number of blocky styrene/maleic anhydride copolymers are commercially available from Sartomer Inc., and are sold under the tradenames SMA2000, SMA3000 and SMA4000. In the case of SMA2000, SMA3000 and SMA4000 the ratio of styrene to maleic anhydride is to 2:1, 3:1 and 4:1 respectively. In these instances, the styrene forms an increasing number of short blocks as the styrene content is increased. SMA2000, SMA3000 and SMA4000 are available as powder, flake or ultrafine powder preparations. Typical molecular weights for SMA2000 are $M_w$ 7,500 ($M_n$ 2,700); for SMA3000 are $M_w$ 9,500 ($M_n$ 3,050) and for SMA4000 are $M_w$ 11,000 ($M_n$ 3,600) as assessed by gel permeation chromatography (GPC).

Styrene/maleic anhydride copolymers must be hydrolysed for use in the present invention, and such hydrolysed polymers may optionally be used in the form of a salt. The polymers may be hydrolysed by a number of means, for example by reflux in aqueous solution, suitably in the presence of a strong base such as sodium hydroxide. Partially hydrolysed styrene/maleic anhydride copolymers may also be of use in the present invention, however, in aqueous solution these are likely to hydrolyse further and for reasons of stability, fully hydrolysed polymer is typically used.

Certain salts of hydrolysed styrene/maleic anhydride copolymers are available commercially, for example, SMA3000HNa is a sodium salt of hydrolysed SMA3000, SMA3000HK is a potassium salt of hydrolysed SMA3000, and SMA4000HNa is a sodium salt of hydrolysed SMA4000. Other salt forms are also available commercially, such as the ammonium salt. Although suitable for use in the present invention, ammonium salts are generally less desirable in cosmetic and pharmaceutical applications due to their associated odours.

A number of styrene/maleic anhydride copolymer half esters are commercially available. These esters may be hydrolysed for use in the present invention. Such half esters include the Sartomer Inc. products known as SMA1440, SMA17352, SMA2625, SMA3840 and SMA3190.

Commercial grades of the styrene/maleic anhydride copolymers, as supplied for industrial uses, may contain monomer, end-capping agent residuals and initiator residuals (e.g. maleic anhydride, styrene, cumene and acetophenone), which residuals are generally undesirable in compositions for use in personal care, cosmetic, pharmaceutical or biomedical products. Residual impurities may be removed or reduced in quantity by means known to those skilled in the art, such techniques include but are not limited to the selective solvation of the residual components into alcohols (for example methanol, ethanol or isopropanol) or into chlorinated solvents (for example chloroform or dichloromethane).

Hydrolysed styrene/maleic anhydride copolymers, i.e. styrene/maleic acid, and salts thereof (e.g. cosmetically and pharmaceutically acceptable salts, such as alkali metal salts, for example potassium or sodium), of use in the present invention will typically have a monomer ratio of styrene to maleic acid of greater than 1:1, in particular greater than 1.2:1, especially greater than 1.5:1, suitably greater than 2.5:1; while additionally typically having a ratio of styrene to maleic acid of less than 4.5:1, especially less than 3.5:1. Exemplary monomer ratios of use in the present invention include: 2:1, 3:1 and 4:1, suitably 2:1 or 3:1. In one embodiment of the invention the ratio of styrene and maleic acid monomer units is 2:1. In a second embodiment of the invention the ratio of styrene and maleic acid monomer units is 3:1.

In one embodiment of the invention the copolymer of styrene and maleic acid (or salt thereof) has an average molecular weight in the range 4,500 to 12,000 and a ratio of styrene to maleic acid of about 2:1, 3:1 or 4:1, in particular about 2:1 or about 3:1.

Although formulations for repeated application to the skin may be slightly acidic, typically being in the pH 5.0-7.5 range, particularly pH 5.5-7.5, formulations for application to other sites, or for internal administration, should typically be maintained around pH 6.5-7.5. Formulations specifically for application to the eye are ideally in the range pH 7.1-7.8, more particularly pH 7.3-7.6 (Carney, L G and Hill, R M *Arch. Opthalmol.* 1976 94(5):821-824). Styrene/maleic acid copolymers with a monomer ratio of styrene to maleic acid of greater than 1:1 and less than 4.5:1 may interact with lipids to form stable macromolecular complexes at pH levels suitable for physiological use (e.g. within the ranges described above). It should be noted that specific embodiments of the invention may not necessarily demonstrate stable polymer and lipid macromolecular assemblies across the entire pH ranges specified.

In one embodiment of the invention the polymer and lipid macromolecular assemblies are stable in aqueous solution at a pH between 5.0-7.5, especially between 5.5-7.5 (e.g. suitable for use in typical formulations for general application to the skin).

In one embodiment of the invention the polymer and lipid macromolecular assemblies are stable in aqueous solution at a pH between 6.5-7.5 (e.g. suitable for use in typical formulations for general application to the body).

In one embodiment of the invention the polymer and lipid macromolecular assemblies are stable in aqueous solution at a pH between 7.1-7.8, especially between 7.3-7.6 (e.g. suitable for use in typical formulations for application to the eye).

Lipids of use in the present invention will typically be membrane forming lipids. Membrane forming lipids comprise a diverse range of structures including phospholipids (for example phosphatidyl choline, phosphatidyl ethanolamine, phosphatidyl glycerol, phosphatidyl inositol and phosphatidyl serine), ceramides and sphingomyelins, among others. Membrane forming lipids typically have a polar head group (which in a membrane aligns towards the aqueous phase) and one or more (e.g. two) hydrophobic tail groups (which in a membrane associate to form a hydrophobic core). The hydrophobic tail groups will typically be in the form of acyl esters, which may vary both in their length (for example from 8 to 26 carbon atoms) and their degree of unsaturation (for example one, two or three double bonds).

Lipids of use in the present invention may be of natural or synthetic origin, and may be a single pure component (e.g. 90% pure, especially 95% pure and suitably 99% pure on a weight basis), a single class of lipid components (for example a mixture of phosphatidyl cholines, or alternatively, a mixture of lipids with a conserved acyl chain type) or may be a mixture of many different lipid types.

In one embodiment of the invention the lipid is a single pure component.

Pure lipids are generally of synthetic or semi-synthetic origin. Examples of pure lipids of use in the present invention include phosphatidyl cholines (for example, DLPC, DMPC, DPPC and DSPC; in particular DLPC, DMPC and DPPC; such as DLPC and DPPC; especially DLPC) and phosphatidyl glycerols (for example DPPG), suitably phosphatidyl cholines. The use of pure lipids is desirable due to their defined composition, however, they are generally prohibitively expensive.

In one embodiment of the invention the lipid is a mixture of components.

Mixtures of lipids of use in the present invention may be of natural origin, obtained by extraction and purification by means known to those skilled in the art. Lipid mixtures of natural origin are generally significantly cheaper than pure synthetic lipids. Naturally derived lipids include lipid extracts from egg or soy, which extracts will generally contain lipids with a mixture of acyl chain lengths, degrees of unsaturation and headgroup types. Exemplary lipid extracts of use in the present invention include: Epikuron 200 available from Degussa Texturant Systems UK Ltd; Emulmetik 950, Emulmetik 930, Pro-Lipo H and Pro-Lipo Duo available from Lucas Meyer Cosmetics SA; Liposome 0041, S 75, S 100, S PC, SL 80 and SL 80-3 available from Lipoid GmbH; Phospholipon® 90H, Phospholipon® 80H, Phospholipon® 90 NG, Nat 8539 available from Phospholipid GmbH. Lipid extracts of plant origin may typically be expected to demonstrate higher levels of unsaturation than those of animal origin. It should be noted that, due to variation in the source, the composition of lipid extracts may vary from batch to batch. Hydrogenated lipids are less prone to peroxidation due to the absence of unsaturation, typically have less coloration and have lower odour.

In one embodiment of the invention the lipid is a lipid extract containing at least 50%, especially at least 75% and suitably at least 90% by weight of phospholipids of a single headgroup type (e.g. phosphatidyl cholines). In a second embodiment of the invention particular lipid extracts may be preferred due to their relatively cheap cost. In a third embodiment of the invention preferred lipid extracts are those which result in solutions of highest clarity. In a fourth embodiment of the invention the lipid is a lipid mixture having a conserved acyl chain length (e.g. at least 50%, especially at least 75% and suitably at least 90% by weight), for example 12 (e.g. lauryl), 14 (e.g. myristyl), 16 (e.g. palmityl) or 18 (e.g. stearyl) carbons atoms in length, in particular 12-16 (e.g. 14 or 16) carbon atoms. In another embodiment of the invention the lipid is a lipid mixture which is hydrogenated (i.e. the acyl chains are fully saturated).

Suitably, a lipid extract of use in the present invention will comprise at least 50% phospholipids by weight (for example, phosphatidyl cholines and phosphatidyl ethanolamines), especially at least 55% phospholipids by weight, in particular at least 60% phospholipids by weight (such as 75% or 90%).

One suitable lipid extract is derived from soy and comprises: at least 92% phosphatidyl cholines, a maximum of 3% lyso-phosphatidyl cholines and a maximum of 2% oils; of which 14-20% of the acyl chains are palmityl, 3-5% stearyl, 8-12% oleic, 62-66% linoleic and 6-8% linolenic. A second suitable lipid extract is derived from soy and comprises: at least 90% hydrogenated phosphatidyl cholines, a maximum of 4% hydrogenated lyso-phosphatidyl cholines and a maximum of 2% oils and triglycerides; of which at least 80% of the acyl chains are stearyl and at least 10% are palmityl.

Lipid mixtures may also be prepared by the combination of pure lipids, or by the combination of one lipid extract with either other lipid extracts or with pure lipids.

It may be desirable to utilise a lipid (either a pure lipid or a lipid mixture) which has a relatively low phase transition temperature, since this may facilitate preparation of compositions of the invention in the absence of heating.

For cosmetic and pharmaceutical applications typically the lipid (for example the pure lipid or the lipid mixture) is one which has been approved for use in cosmetic and/or pharmaceutical applications as appropriate.

Those skilled in the art will recognise that lipid mixtures of use in the invention may comprise non-membrane forming lipid components (e.g. cholesterol), or may in some circumstances be a mixture of only non-membrane forming lipids which in combination demonstrate membrane forming ability and a suitability for use in the invention.

The suitability of a particular pure lipid or lipid mixture for use in the present invention may be determined by those skilled in the art by routine experimentation based on the guidance provided herein.

Typically the ratio of polymer to lipid in the compositions of the present invention will be greater than 1:2 on a weight basis, especially greater than 1:1 (for example about 1.5:1 or 2.5:1). Suitably the ratio of polymer to lipid in the compositions of the present invention will be greater than 1.25:1. Insufficient quantities of polymer may result in solutions with sub-optimal clarity. Excess quantities of polymer may result in an increased solution viscosity (which may or may not be a desirable feature depending upon the specific application). Suitably the ratio of polymer to lipid in the compositions of the present invention will be less than 100:1, such as less than 25:1, in particular less than 10:1 (e.g. less than 5:1).

The presence of a small quantity of cosurfactant material may enhance the ability of the styrene/maleic acid copolymer to solubilise lipid (in particular lipid mixtures). This cosurfactant can take the form of a low molecular weight material, such as the naturally occurring lyso-phospatidyl choline (lyso-PC) which is available under the tradename S LPC from Lipoid GmbH, or a polymeric surfactant material, such as the synthetic block copolymer polyoxyethylene/polyoxypropylene known as a poloxamer and supplied by BASF Corporation (e.g. the specific grade known under the tradename Lutrol® F127). The cosurfactant may also be a combination of more than one surfactant. Suitably cosurfactant is added in an amount equivalent to between 0.1-5% of the weight of lipid in the composition, especially 0.5-2.5% and in particular 0.75-1.5% (for example about 1%). In one embodiment of the invention the cosurfactant is a block copolymer of polyoxyethylene/polyoxypropylene (for example having a molecular weight of 5000 to 15000 Da, in particular 10000 to 13000 Da, such as around 12600 Da as is found in Lutrol® F127). In a second embodiment of the invention the cosurfactant is lyso-PC. It may be noted that certain lipid extracts may already contain lyso-PC, however, this does not preclude the addition of a cosurfactant.

Lyso-PC as a cosurfactant may be added either in its pure form (e.g. S LPC from Lipoid GmbH), or as one component of a lipid mixture (e.g. a high lyso-PC content lecithin, such as those having at least 10% lyso-PC content by weight, especially at least 15% lyso-PC by weight). An exemplary high lyso-PC content lecithin is SL 80-3 from Lipoid GmbH.

Lipid mixtures (such as lipid extracts) which already contain a high lyso-PC content do not generally benefit significantly from the addition of further lyso-PC as a cosurfactant. As such, the need for a cosurfactant can be avoided simply by the selection of a lipid mixture which already contains a sufficient quantity of lyso-PC.

The compositions of the present invention may be in the form of an aqueous solution, especially a stable clear aqueous solution, suitably a stable clear and colourless aqueous solution. However, for ease of transportation and handling, once prepared, the compositions may be freeze-dried to form a dry powder which has the benefits of being lower in both volume and weight. In one embodiment of the present invention the composition is in the form of an aqueous solution. In a further embodiment of the present invention the composition is in freeze-dried form (for example as a powder, resin or flake, especially as a powder or flake, in particularly as a powder). Aqueous solutions include aqueous semi-solids such as gels. Aqueous solutions of compositions according to the present invention may be prepared at relatively high concentrations, for example concentrations of 30% by weight have been prepared from reconstituted freeze-dried compositions containing the active agent TECA. High concentrations may demonstrate an increased viscosity. In one embodiment of the invention there is provided an aqueous solution comprising 0.001-10% by weight of the compositions of the invention (the percentage being determined by the dry weight of composition of the invention relative to the total weight of composition and water). In a second embodiment of the invention there is provided an aqueous solution comprising 10-20% by weight of the compositions of the invention. In a third embodiment of the invention there is provided an aqueous solution comprising greater than 20% by weight of the compositions of the invention.

Compositions of the present invention may suitably be prepared by mixing a solution of a styrene/maleic acid copolymer, wherein the copolymer of styrene and maleic acid is non-alternating, with an aqueous emulsion containing lipid, and if necessary adjusting the pH of the resulting mixture such that the polymer/lipid macromolecular assemblies form.

Other compositions of the present invention may suitably be prepared by mixing a solution of a styrene/maleic acid copolymer having a ratio of styrene to maleic acid monomers of greater than 1:1, with an aqueous emulsion containing lipid, and if necessary adjusting the pH of the resulting mixture such that the polymer/lipid macromolecular assemblies form.

The polymer solution may be prepared by dissolving the polymer in water, optionally with stirring and heating (for example to approximately 50° C.). The lipid emulsion may be prepared by mixing dried lipid with water under stirring and heating (suitably to a temperature above the phase transition temperature of the lipid component, for example approximately 50° C.), followed by homogenisation. Suitably the polymer solution and lipid emulsion are mixed by the addition (e.g. the slow addition) of lipid emulsion to the polymer solution, optionally together with heating (e.g. to around 50° C.).

The pH of solutions may be adjusted using acids or bases as appropriate. Compositions for use in the fields of cosmetics or pharmaceuticals will typically utilise acids and/or bases which are physiologically acceptable. Physiologically acceptable acids include hydrochloric acid. Physiologically acceptable bases include sodium or potassium hydroxide, suitably sodium hydroxide.

Cosurfactant, when present, will typically be mixed with lipid prior to the formation of the aqueous emulsion.

In a further aspect of the present invention there is provided a method for the production of a composition comprising lipid and a copolymer of styrene and maleic acid, wherein the copolymer of styrene and maleic acid is non-alternating, wherein the polymer and lipid are in the form of macromolecular assemblies, comprising the steps of:
 (i) Preparing an aqueous solution of a copolymer of styrene and maleic acid, wherein the copolymer of styrene and maleic acid is non-alternating;
 (ii) Preparing an aqueous lipid emulsion;
 (iii) Mixing the aqueous lipid emulsion and aqueous solution of copolymer;
 (iv) Adjusting the pH of the mixture, if necessary, such that polymer/lipid macromolecular assemblies form.

If desirable, a further optional step of removing the water may be performed.

In a further aspect of the present invention there is provided a method for the production of a composition comprising lipid and a copolymer of styrene and maleic acid, wherein the ratio of styrene to maleic acid monomer units is greater than 1:1, wherein the polymer and lipid are in the form of macromolecular assemblies, comprising the steps of:
 (i) Preparing an aqueous solution of a copolymer of styrene and maleic acid, wherein the ratio of styrene to maleic acid monomer units is greater than 1:1;
 (ii) Preparing an aqueous lipid emulsion;
 (iii) Mixing the aqueous lipid emulsion and aqueous solution of copolymer;
 (iv) Adjusting the pH of the mixture, if necessary, such that polymer/lipid macromolecular assemblies form.

If desirable, a further optional step of removing the water may be performed.

Compositions of the present invention in the form of an aqueous solution may be freeze-dried to produce compositions of the present invention in the form of a freeze-dried powder. Freeze-dried compositions may be readily reconstituted into aqueous solution by the addition of water with stirring and warming. The durability of compositions of the present invention to freeze-drying may be improved by the addition of protectants, for example sugars, such as trehalose (alpha,alpha-D-trehalose dihydrate, available from CMS Chemicals Ltd (UK)).

Water may be removed by other means, such as rotary evaporation under reduced pressure and at an elevated temperature (e.g. 65-75° C.).

One use of compositions of the invention is as a solubilising agent.

Solubilising agents may be of use as formulating aids, solubilising active agents which have poor aqueous solubility (for example aqueous solubility of less than 1% w/w, suitably less than 0.1% w/w or less than 0.01% w/w). Solubilising agents may also be of use as carriers for active agents which preferentially partition into the solubilising agent (for example, active agents which partition into octanol as opposed to water). The active agent may for example be a medicament for the treatment or prevention of a medical disorder, or alternatively may be a cosmetic agent or an agent which is applied for cosmetic purposes.

Active agents having poor aqueous solubility include the oil-soluble vitamins (including vitamins A, D, E and K) and oil soluble derivatives of water soluble vitamins (including vitamin C), which are frequently applied to the skin as part of water-in-oil or oil-in-water emulsions as antioxidants, depigmenting agents, moisturisers, collagen stimulators, anti-aging, anti-wrinkle and anti-inflammatory agents.

The vitamin A family includes retinol, retinol palmitate, retinol acetate, and related retinoids, and also pro-vitamin A, such as β-carotene. Oil-soluble derivatives of vitamin C include ascorbyl palmitate, ascorbyl dipalmitate and ascorbyl tetraisopalmitate (in particular ascorbyl palmitate and ascorbyl dipalmitate). Vitamin D and its derivatives include cholecalciferol/calcitriol (vitamin $D_3$), calcipotriol and tacalcitol (in particular cholecalciferol), which may be used in the treatment of psoriasis. Vitamin K series, including $K_1$ (phytonadione), may be used in the treatment of bruised skin and in the repair of capillary damage. 7-dehydrocholesterol is a pre-cursor for vitamin D.

A large number of active agents demonstrating a poor aqueous solubility are based around a triterpenoid or steroidal nucleus. Many of these agents have potent biological activity and are widely used in cosmetics and pharmaceuticals.

Oil-soluble actives based upon a triterpenoid structure include natural extracts (for example from *Centella asiatica* (Hydrocotyl), such as TECA, asiaticoside, asiatic acid and madecassic acid (in particular TECA, alternatively asiaticoside), which are of use in regulating and activating collagen synthesis; or liquorice extracts such as glabridin, which is of use as an anti-tyrosinase and anti-microbial, and licochalcone A, which is of use as an inhibitor of 5-alpha-reductase and as an anti-microbial). Additional actives include extracts from *Aesculus* (Horse chestnut). Other actives include escin (a triterpenoid) and esculoside (esculin, a coumarin). Further glycoside actives include extracts from *Ruscus* (Butcher's broom), including ruscogenin and neuroruscogenin. Triterpenoid extracts of Boswellia (Frankincense) including Boswellin® CG from Sabinsa Corporation USA are also examples of actives in this class. Other oil-soluble actives based upon a steroidal structure include those used to treat inflammatory conditions (such as hydrocortisone, clobetasone butyrate, hydrocortisone butyrate, clobetasol propionate, fluticasone propionate and dexamethasone, in particular hydrocortisone, clobetasone butyrate, hydrocortisone butyrate, clobetasol propionate and dexamethasone) and hormones (such as testosterone, oestrogen and oestrogens). Additional steroidal compounds include dexamethasone acetate anhydride, hydrocortisone acetate and cortisone acetate. Steroidal like compounds include cholesterol and cholesterol potassium sulphate which may, for example, be used in moisturising.

Other active agents include soy isoflavones; liquorice extracts, such as Licorice CG from Sabinsa Corporation USA, P-U and PT-40 from Maruzen Pharmaceuticals Co. Ltd. Japan.

Endogenous skin lipids, including ceramides (e.g. ceramide IIIA) have poor aqueous solubility and are of use as skin moisturisers and whitening agents. Other ceramides include ceramide IIIB and synthetic ceramides, such as ceramide HO3 from Sederma, France.

Other relatively oil-soluble actives include lawsone (2-hydroxy-1,4-naphthoquinone), natural henna extract of *Lawsonia alba*, caffeine and minoxidil.

Antimicrobial active agents include: anti-bacterials, such as erythromycin, neomycin (e.g. as the sulphate); anti-fungals, such as ciclopirox olamine, piroctone olamine (each of which are examples of pyridone antifungals), clotrimazole, fluconazole, econazole, ketaconazole and nystatin (in particular piroctone olamine, clotrimazole, ketaconazole and nystatin).

Oil-soluble derivatives of active agents which have a peptide structure include Matrixyl™ (palmitoyl-KTTKS, which downregulates collagenase and therefore increases collagen production) and Argireline® (acetyl hexapeptide-3, which inhibits acetylcholine binding, decreasing the strength of neuromuscular signals and thus decreasing muscle contraction).

Further oil-soluble active botanical extracts include rosmarinic acid and green tea extract from Sabinsa Corporation USA, nettle extracts and ginkgo extracts.

Cosmoperine® from Sabinsa Corporation USA is an oil-soluble penetration enhancer.

An oil-soluble anti-oxidant is NDGA (nordihydroguaiaretic acid) from Whyte Chemicals UK.

Another class of active agents includes sunscreens. Exemplary sunscreens include octyl methoxycinnamate, benzophenone 3,3-benzylidene camphor, avobenzene, para-aminobenzoic acid (PABA) and galanga (ethylhexyl paramethoxy cinnamate).

A still further class of active agents is essential oils including a melaleucole oil and peppermint oil and fragrances including Unisex Bouquet (AFL-3607/A), Apricosal (AFL-3607/E) and Fougere (AFL-3607/D) supplied by Arriva Fragrances, UK.

A still further class of active agents is coolants and natural moisturizing agents such as Questice CQ U/A (Menthyl PCA) supplied by Quest International, UK.

Another class of active agents is dyes.

The quantity of active agent which may be combined with and solubilised in the compositions of the present invention will typically be in the range of 0.001-50% of the weight of polymer and lipid, especially in the range of 0.001-25% (e.g. 5-20%).

In a further aspect of the present invention there is provided a formulation comprising a composition of the invention, and which further comprises an active agent. In one embodiment of the invention the active agent is an oil soluble vitamin or oil soluble vitamin derivative (for example ascorbyl palmitate, ascorbyl dipalmitate and ascorbyl tetraisopalmitate, in particular ascorbyl palmitate and ascorbyl dipalmitate). In a second embodiment of the invention the active agent has a triterpenoid (e.g. TECA or asiatic acid) or steroidal nucleus. In a third embodiment of the invention the active agent is an oil soluble peptide (e.g. palmityl-KTTKS or acetyl hexapeptide-3). In a fourth embodiment of the invention the active agent is a sunscreen.

Active agents may be conveniently incorporated into the compositions of the present invention by the addition of the active agent to the lipid (and where appropriate to the lipid and cosurfactant) prior to the preparation of the aqueous lipid emulsion, and before the emulsion and polymer solution are mixed.

There is provided an aqueous formulation comprising a composition of the invention, and which further comprises an active agent.

In an analogous manner to compositions of the invention, aqueous formulations of the present invention (which comprise an active agent) may generally be freeze-dried and reconstituted as necessary. As such, also provided is a formulation comprising a composition of the invention, and which further comprises an active agent, which is in freeze-dried form (for example as a powder, resin or flake, in particular powder or flake).

In general a formulation of the present invention will be incorporated into a cosmetic or pharmaceutical preparation which is tailored to suit the particular purpose, manner of use and mode of administration. Formulations may be mixed with one or more cosmetic or pharmaceutically acceptable carriers or excipients (anti-oxidants, preservatives, viscosity modifiers, colourants, flavourants, perfumes, buffers, acidity regulators, chelating agents, or other excipients), and optionally with other therapeutic ingredients if desired. Such preparations may be prepared by any of the methods known in the art, and may for example be designed for inhalation, topical or parenteral (including intravenous, intra-articular, intra-muscular, intra-dermal and subcutaneous) administration.

Preparations for systemic delivery are suitably made using low molecular weight copolymer, although this polymeric material is non-degradable, the butyl half ester has previously been used in medicine and is likely to be readily excreted through the kidneys. Some of the phospholipids described in this application are used for parenteral nutrition and are likely to be broken down fairly readily in the body without causing serious problems. Preparations for parenteral delivery will suitably be sterile.

Compositions of the present invention are believed to be particularly suitable for the delivery of active agents to the skin.

When delivering active agents to the skin it is generally important that the particle size be less than that of the lipid interstices found between the corneocytes within the outer layer of the skin, in order for the material to be adequately absorbed into the stratum corneum. The inter-corneocyte interstices have a thickness in the region of 50-100 nm, hence, particles (for example the macromolecular assemblies of the present invention) should desirably to be sized less than 100 nm, especially less than 50 nm and more particularly less than 25 nm in order to be absorbed efficiently. Hydrophilic pores/spaces between the corneocytes and the lipid lamellae layers within the skin are substantially smaller than the lipid interstices, starting in the order of 0.4 nm but having an ability to enlarge to around 20-30 nm in diameter (Cevc, G *Advanced Drug Delivery Reviews* 2004 56:675-711). The novel macromolecular assemblies described in this application may be well suited to penetrating the inter-corneocyte lipid layer and also the hydrophilic pores, and could therefore be used to deliver oily materials e.g. active agents. Since the macromolecular assemblies may be trapped within the stratum corneum, they may act as reservoirs for active agents to enable sustained release into the deeper layers of the skin and thereby provide a distinct therapeutic profile. Advantageously, this could improve product efficacy, reduce the number of applications and quantity of active agent required, and would be more convenient for the consumer or patient.

Preparations for topical application may include, for example, anti-oxidants (e.g. alpha-tocopherol, butylated hydroxyanisole (BHA) or butylated hydroxytoluene (BHT)), preservatives (e.g. 2-phenoxyethanol, sorbic acid or parabens), viscosity modifiers (e.g. water soluble gums and resins, such as xanthan gum, or lightly cross-linked synthetic polymers such as carbopols), colourants, flavourants, perfumes, buffers, acidity regulators, chelating agents (e.g. such as EDTA, sodium edetate, disodium edetate or calcium disodium edetate), penetration enhancers and anti-tack agents. Suitable carbomers include Carbopol®980 and Ultrez® 20.

Preparations for topical application may be incorporated into hydrogel patches (i.e. 3-dimensional gels of fixed structure). Application utilising hydrogels may be advantageous in that: (i) the hydrogel patch may act as a convenient repository for prolonged administration and/or (ii) the hydrogel patch may provide a quantifiable dosage form, such that the quantity of active agent administered can be effectively controlled.

Thus, there is provided a cosmetic preparation comprising a composition of the invention and an active agent, and which further comprises a cosmetically acceptable carrier or excipient.

There is also provided a pharmaceutical preparation comprising a composition of the invention and an active agent, and which further comprises a pharmaceutically acceptable carrier or excipient.

Accordingly, there is also provided a composition of the invention for use in therapy.

In a further aspect of the present invention there is provided the use of a composition of the invention as a solubilising agent, for example in the solubilisation of an active agent (e.g. an oil soluble vitamin or oil soluble vitamin derivative, an agent having triterpenoid or steroidal nucleus, or an oil soluble peptide). Other active agents which may be solubilised include terpenoids.

Other potential uses of compositions of the present invention include use as a means of solubilising membrane peptides or proteins for the investigation of their structure. A need has been identified for solubilising agents that can be used for solubilising membrane peptides and proteins (including integral, membrane tethered or membrane associated proteins, for example drug receptor proteins), within phospholipid membranes in such a way as to retain their native conformation and thereby to enable their structure to be investigated (e.g. by NMR spectroscopy).

In addition to structural investigations, it may also be desirable to investigate the interactions of membrane proteins and peptides with other species. Such other species may also be membrane peptides and proteins. In the case of membrane receptors such other species include ligands and ligand fragments (e.g. agonists and antagonists). In the case of enzymes, such other species may be ligands and ligand fragments (e.g. substrate(s) and inhibitors). Other membrane bound or membrane associated molecules which may be the subject of investigations include glycolipids.

In addition to NMR, there are many other suitable spectroscopic techniques which are well known to those skilled in the art for the purposes of investigating peptides and proteins (including x-ray crystallography, infra-red spectroscopy and circular dichroism).

Numerous techniques exist for the transfer of membrane proteins from a detergent solubilised state to a lipid bilayer state. For example, biobeads may be used to remove detergent and thereby promote transfer but other techniques can also be used, such as freeze-thawing. Freeze-thawing is a widely used technique in the membrane protein community, involving rapid freeze (using for example liquid nitrogen) and thaw (e.g. 37° C.) cycles (which are repeated multiple times, for example 4 times) which causes the membrane proteins to incorporate into macromolecular assemblies of the invention. The most suitable technique for incorporating a particular protein may vary, depending on the absolute and critical micellar concentration of the detergent used.

Compositions of the present invention may offer an advantage over the use of bicelles (Sanders, C R and Landis, G C *Biochemistry* 1995 34(12):4030-4040) for the purpose of reconstituting membrane peptides and proteins.

Accordingly, there is provided the use of a composition of the invention for the solubilisation of a membrane peptide or protein. Also provided are compositions of the invention (e.g. in dry or aqueous form) which further comprise a membrane peptide or protein.

There is also provided a method for the solubilisation of a membrane peptide or protein which comprises forming a composition of the invention which comprises said membrane peptide or protein.

Further, there is provided a method for the screening of candidate agents for interaction with a membrane protein or peptide comprising the steps of:
  (i) solubilising a membrane protein or peptide in a composition of the invention;
  (ii) testing a candidate agent to determine whether it interacts with the solubilised membrane protein or peptide.

Candidate agents may be putative ligands or ligand fragments (e.g. agonists, antagonists, inhibitors and such).

It may also be envisaged that the compositions of the present invention may be used to solubilise peptides or proteins which are immunogenic in nature (e.g. antigens). Alternatively, it may be noted that WO95/11700 discloses an oil-in-water submicron emulsion (SME) for use as a vaccine adjuvant for enhancing immunogenicity and improving the immune response of antigens in vaccines. Compositions of the present invention may also be of use as particulate vaccine adjuvants.

Furthermore, there is a need for treatment of medical conditions affecting mucosal surfaces, e.g. for ophthalmic use such as in the treatment of the condition known as "dry eye" syndrome, and for lubricating biological membranes (e.g. synovial). The tear film has a coating of phospholipids, which are necessary for the formation of a stable tear film. Diseases where the tear film is deficient may potentially be treated by the addition of an aqueous phospholipid solution, such as an aqueous solution of the compositions of the present invention. Compositions of the present invention are advantageous in this regard, since they are clear and colourless, unlike conventional aqueous preparations of phospholipids which may be opaque.

There is also a need for lubricating phospholipids to treat the surfaces of articulated joints in connection with arthritic conditions or to lubricate surfaces of medical devices and prostheses, e.g. artificial joints and contact lenses, that are fitted into or on the body, or to prevent focal adhesions between tissues such as those that may occur during surgical procedures. Compositions of the present invention may be of use in this regard (e.g. by intra-articular injection).

The compositions of the invention may also have the ability to deliver active agents locally to the lung or, via the highly permeable membranes lining the deep lung, into the systemic circulation. The similarity between the phospholipid compositions of the invention and the surfactant fluid lining the internal alveolar and bronchial surfaces of the lung may ensure that the compositions of the invention are suited to deliver active agents to the lung, especially the deep lung, or to act as a means of delivering phospholipid to the lung for the treatment of neonatal or adult respiratory distress syndrome, a condition characterised by a insufficient levels of native lung surfactant or phospholipids. Delivery to the lung may be by aerosol or by nebulisation.

The following Examples are non-limiting and are provided to illustrate the preparation and use of compositions according to the present invention such that a person skilled in the art may more readily appreciate the nature of the invention and put the invention into practical effect.

COMPARATIVE EXAMPLES

Comparative Example 1

The Ability of Common Surfactants to Solubilise Lipids

The ability of four commonly used surfactants to solubilise a number of lipid mixtures was tested for the purpose of comparison with the solubilising compositions of the present invention.

Method

The appropriate quantity of double strength lipid emulsion was prepared by heating to approximately 50° C. and stirred until a uniform emulsion was formed. The mixture was then homogenised for 10 minutes. Surfactant was added to water to form a double strength stock solution, to which an equal quantity of lipid emulsion was then added dropwise under stirring and heating.

Percentage values specified in this experiment refer to the weight of the component in question as a proportion of the total weight of the composition.

Once the mixtures were prepared they were visually examined to determine whether the surfactant component had solubilised the lipid component in the aqueous medium. The clarity of a mixture was categorised as being clear if there was no significant visible opacity to the naked eye, whereas a mixture was categorised as cloudy if there was significant visible disruption to the passage of light.

Surfactants

Sodium dodecyl sulphate (CAS Ref 151-21-3), often referred to by the acronym SDS, is one of the most widely used anionic surfactants, for example it is used in many general purpose cleaning agents. SDS was utilised as a laboratory reagent grade powder.

Mackanate DC30 is produced by the McIntyre Group Ltd (USA) and is known by the generic name disodium dimethicone copolyol sulphosuccinate. Mackanate is a mild anionic surfactant used in personal care cleaning agents. Mackanate was supplied as a clear liquid at 30% concentration.

Lutrol® F127 (CAS Ref 9003-11-6), known by the generic name poloxamer 407, is produced by BASF and is a polyoxyethylene/polyoxypropylene block copolymer surfactant. F127 is a non-ionic polymeric surfactant, possessing 70% polyethylene oxide content, average molecular weight of 12,600 and supplied as a powder. Having a low dermal and ocular irritancy, F127 is of widespread use in personal care applications.

Lyso-phosphatidyl choline (CAS Ref 9008-30-4), is available under the tradename S LPC from Lipoid GmbH. Structurally related to phosphatidylcholines, it differs in that it contains only one fatty acid chain, resulting in a much higher surface activity. S LPC is used as a mild emulsifier in personal care applications. S LPC used herein was at 93.9% purity and supplied as a powder.

Lipids

Phospholipon® 90H, referred to herein by the abbreviation 90H, available from Phospholipid GmbH (Germany), is a hydrogenated soy lecithin extract of at least 90% phosphatidyl choline content and is approved for pharmaceutical and cosmetic use. It is generally used as an emulsifier and is known to form liposomes.

Pro-LipoH, referred to herein by the abbreviation ProH, is a hydrogenated soy phospholipid gel concentrate containing 20% phosphatidyl choline with a water, alcohol and glycerine content of 80%. It is a proliposomal composition and is available from Lucas Meyer Cosmetics SA. The use of ProH for pharmaceutical applications is covered by EP0158441.

Results

Table 1 below summarises the results of the experiment.

TABLE 1

The ability of common surfactants to solubilise lipids

| Surfactant Component | Surfactant Concentration % | Lipid Component | Lipid Concentration* % | Clarity |
|---|---|---|---|---|
| SDS | 2.5% | 90 H | 1% | Cloudy |
| SDS | 5.0% | 90 H | 1% | Clear |
| SDS | 2.5% | ProH | 1% | Clear |
| SDS | 5.0% | ProH | 1% | Clear |
| Mackanate | 2.5% | 90 H | 1% | Cloudy |
| Mackanate | 5.0% | 90 H | 1% | Cloudy |
| Mackanate | 2.5% | ProH | 1% | Cloudy |
| Mackanate | 5.0% | ProH | 1% | Cloudy |
| F127 | 2.5% | 90 H | 1% | Cloudy |
| F127 | 5.0% | 90 H | 1% | Cloudy |
| F127 | 2.5% | ProH | 1% | Cloudy |
| F127 | 5.0% | ProH | 1% | Cloudy |
| S LPC | 2.5% | 90 H | 1% | Cloudy |
| S LPC | 5.0% | 90 H | 1% | Cloudy |

TABLE 1-continued

The ability of common surfactants to solubilise lipids

| Surfactant Component | Surfactant Concentration % | Lipid Component | Lipid Concentration* % | Clarity |
|---|---|---|---|---|
| S LPC | 2.5% | ProH | 1% | Clear |
| S LPC | 5.0% | ProH | 1% | Clear |

*Quantity of Pro H utilised is 5%, such that 1% lipid is present in the final preparation and 4% alcohol and glycerine.

As can be seen from the data in Table 1, in general, conventional surfactants at a concentration of 5% w/w are not capable of solubilising lipids at a concentration of 1.0% w/w to form clear and colourless solutions. However, SDS and S LPC both produced clear and colourless solutions at 2.5% concentration when the lipid used was Pro H, and SDS produces a clear and colourless solution at 5% concentration when the lipid is 90H. Pro H may be considered as an atypical example of a lipid because of its pre-processed form, and its residual alcohol content.

Comparative Example 2

The Ability of Common Surfactants to Solubilise Active Agents

The ability of four commonly used surfactants to solubilise an exemplary active agent having poor water solubility was tested for the purpose of comparison with the solubilising compositions of the present invention.

Method

The appropriate quantity of surfactant and active agent was added to water, which was then warmed to approximately 50° C. and stirred. The mixture was then homogenised for 10 minutes.

Percentage values specified in this experiment refer to the weight of the component in question as a proportion of the total weight of the composition.

Once the mixtures were prepared they were visually examined to determine whether the surfactant component had solubilised the active agent in the aqueous medium. The clarity of a mixture was categorised as being clear if there was no significant visible opacity to the naked eye, whereas a mixture was categorised as cloudy if there was significant visible disruption to the passage of light.

Surfactants

The four surfactants (SDS, Mackanate, F127 and S LPC) were as described above in Comparative Example 1.

Active Agent

Titrated extract of *Centella asiatica*, referred to herein as TECA, is available from Roche Nicholas Laboratories SA—Serdex Division (France), now Bayer Santé Familiale. TECA is a mixture of 54-66% (i.e. around 60%) free genins (asiatic acid and madecassic acid) and 36-44% (i.e. around 40%) asiaticoside, of use in regulating collagen synthesis, wound healing, anti-wrinkle, toning and anti-cellulite treatments. Pharmaceutical grade (95% purity) was utilised, supplied as a powder.

Results

Table 2 below summarises the results of the experiment.

TABLE 2

The ability of common surfactants to solubilise active agents

| Surfactant Component | Surfactant Concentration % | Active Agent | Active Agent Concentration % | Clarity |
|---|---|---|---|---|
| SDS | 5 | TECA | 0.5 | Cloudy |
| MACKANATE | 5 | TECA | 0.5 | Cloudy |

TABLE 2-continued

The ability of common surfactants to solubilise active agents

| Surfactant Component | Surfactant Concentration % | Active Agent | Active Agent Concentration % | Clarity |
|---|---|---|---|---|
| F127 | 5 | TECA | 0.5 | Cloudy |
| S LPC | 5 | TECA | 0.5 | Cloudy |

Exemplary conventional surfactants, at the tested concentrations, were unable to solubilise an exemplary active agent which has a poor water solubility.

Comparative Example 3

The Ability of Lipids to Solubilise Active Agents

The ability of three lipid compositions to solubilise an exemplary active agent having poor water solubility was tested for the purpose of comparison with the solubilising compositions of the present invention.

Method

The appropriate quantity of lipid and active agent was added to water, which was then warmed to approximately 50° C. and stirred until a uniform emulsion was formed. The emulsion was then homogenised for 10 minutes.

Percentage values specified in this experiment refer to the weight of the component in question as a proportion of the total weight of the composition.

Once the mixtures were prepared they were visually examined to determine whether the lipid component had solubilised the active agent in the aqueous medium. The clarity of a mixture was categorised as being clear if there was no significant visible opacity to the naked eye, whereas a mixture was categorised as cloudy if there was significant visible disruption to the passage of light.

Lipids

The three lipid compositions (90H, Pro H and Em930) were as described above in Comparative Example 1.

Active Agent

The exemplary active agent, TECA, was as described in Comparative Example 2.

Results

Table 3 below summarises the results of the experiment.

TABLE 3

The ability of lipids to solubilise active agents

| Lipid Component | Lipid Concentration* % | Active Agent | Active Agent Concentration % | Clarity |
|---|---|---|---|---|
| 90H | 1.0 | TECA | 0.5 | Cloudy |
| Pro H | 1.0 | TECA | 0.5 | Cloudy |
| Em930 | 1.0 | TECA | 0.5 | Cloudy |

*Quantity of Pro H utilised is 5%, such that 1% lipid is present in the final preparation and 4% alcohol and glycerine.

The three exemplary lipid compositions did not interact with TECA at the tested concentrations to form clear and colourless aqueous solutions.

Comparative Example 4

The Ability of Blocky Styrene/Maleic Acid Copolymers to Solubilise Active Agents The ability of an exemplary blocky styrene/maleic acid copolymer (i.e. hydrolysed styrene/maleic anhydride copolymer) to solubilise an exemplary active agent having poor water solubility was tested for the purpose of comparison with the solubilising compositions of the present invention.

Method

A double strength aqueous stock solution of blocky styrene/maleic acid polymer was prepared. To this, an equal volume of a double strength aqueous emulsion of TECA was added, to provide a final mixture containing the desired concentrations of both components. This mixture was warmed to approximately 50° C. and stirred for a further 20 minutes, before being homogenised for 10 minutes.

Percentage values specified in this experiment refer to the weight of the component in question as a proportion of the total weight of the composition.

Once the mixtures were prepared they were visually examined to determine whether the polymer component had solubilised the active agent in the aqueous medium. The clarity of a mixture was categorised as being clear if there was no significant visible opacity to the naked eye, whereas a mixture was categorised as cloudy if there was significant visible disruption to the passage of light.

Polymer

SMA3000 HNa was obtained from Sartomer Inc., it is a sodium salt form of hydrolysed SMA3000 (i.e. a styrene/maleic acid sodium salt) and contains a 3:1 ratio of styrene to maleic acid monomer units (i.e. is a blocky polymer). The polymer is supplied as a resin.

Active Agent

The exemplary active agent, TECA, was as described in Comparative Example 2.

Results

Table 4 below summarises the results of the experiment.

TABLE 4

The ability of blocky styrene/maleic acid copolymers to solubilise active agents

| Polymer Component | Polymer Concentration % | Active Agent | Active Agent Concentration % | Clarity |
|---|---|---|---|---|
| SMA 3000HNa | 2.5 | TECA | 0.5 | Cloudy |
| SMA 3000HNa | 5.0 | TECA | 0.5 | Cloudy |

SMA3000 HNa, a blocky styrene/maleic acid copolymer containing a 3:1 ratio of styrene to maleic acid monomer units, was unable to solubilise the exemplary active agent to produce clear and colourless aqueous solutions at the concentrations tested.

Comparative Example 5

The Ability of Lipid and Surfactant Mixtures to Solubilise Active Agents

The ability of lipid and surfactant mixtures to solubilise an exemplary active agent having poor water solubility was tested for the purpose of comparison with the solubilising compositions of the present invention.

Method

The appropriate quantities of lipid, surfactant and active agent were added to water, which was then warmed to approximately 50° C. and stirred until a uniform emulsion was formed. The mixture was then homogenised for 10 minutes.

Percentage values specified in this experiment refer to the weight of the component in question as a proportion of the total weight of the composition.

Once the mixtures were prepared they were visually examined to determine whether the lipid and surfactant mixture had solubilised the active agent in the aqueous medium. The clarity of a mixture was categorised as being clear if there was no significant visible opacity to the naked eye, whereas a mixture was categorised as cloudy if there was significant visible disruption to the passage of light.

Surfactants

F127 and S LPC were as described above in Comparative Example 1.

SDS was as described above in Comparative Example 1.

Lipid 90H was as described above in Comparative Example 1.

Active Agent

The exemplary active agent, TECA, was as described in Comparative Example 2.

Results

Table 5 below summarises the results of the experiment.

TABLE 5

The ability lipid and surfactant mixtures to solubilise active agents

| Lipid Component | Lipid Concentration % | Surfactant Component | Surfactant Concentration % | Active Agent | Active Agent Concentration % | Clarity |
|---|---|---|---|---|---|---|
| 90H | 1.0 | F127 | 0.01 | TECA | 0.5 | Cloudy |
| 90H | 1.0 | S LPC | 0.01 | TECA | 0.5 | Cloudy |
| 90H | 1.0 | SDS | 2.5% | TECA | 0.5 | Cloudy |
| 90H | 1.0 | SDS | 5% | TECA | 0.5 | Clear |

The results in Table 5 indicate that the lipid and a small quantity of surfactant alone do not have sufficient solubilising ability to form clear and colourless aqueous solutions of the exemplary active agent.

SDS is a powerful surfactant and it is not surprising that at high concentration it is capable of solubilising TECA and lipid. However, at a concentration of 2.5% w/w SDS is not able to form clear and colourless solutions of the active agent and lipid.

Comparative Example 6

The Ability of Blocky Styrene/Maleic Acid Copolymers and Surfactant to Solubilise Active Agents The ability of an exemplary blocky styrene/maleic acid copolymer (i.e. hydrolysed styrene/maleic anhydride copolymer) and surfactant mixture to solubilise an exemplary active agent having poor water solubility was tested for the purpose of comparison with the solubilising compositions of the present invention.

Method

A double strength aqueous stock solution of blocky styrene/maleic acid polymer was prepared. To this, an equal volume of a double strength aqueous emulsion of surfactant and TECA was added, to provide a final mixture containing the desired concentrations of each component. This mixture was warmed and stirred for a further 20 minutes.

Percentage values specified in this experiment refer to the weight of the component in question as a proportion of the total weight of the composition.

Once the mixtures were prepared they were visually examined to determine whether the polymer and surfactant had solubilised the active agent in the aqueous medium. The clarity of a mixture was categorised as being clear if there was no significant visible opacity to the naked eye, whereas a mixture was categorised as cloudy if there was significant visible disruption to the passage of light.

Polymer

SMA3000 HNa was as described in Comparative Example 4.

Surfactants

F127 and S LPC were as described in Comparative Example 1.

Active Agent

The exemplary active agent, TECA, was as described in Comparative Example 2.

Results

Table 6 below summarises the results of the experiment.

TABLE 6

The ability of blocky styrene/maleic acid copolymers and surfactant to solubilise active agents

| Polymer Component | Polymer Concentration % | Surfactant Component | Surfactant Concentration % | Active Agent | Active Agent Concentration % | Clarity |
|---|---|---|---|---|---|---|
| SMA 3000HNa | 2.5 | F127 | 0.01 | TECA | 0.5 | Cloudy |
| SMA 3000HNa | 2.5 | S LPC | 0.01 | TECA | 0.5 | Cloudy |

SMA3000 HNa, a blocky styrene/maleic acid copolymer containing a 3:1 ratio of styrene to maleic acid monomer units, and a small quantity of surfactant were unable to solubilise the exemplary active agent to produce clear and colourless aqueous solutions at the concentrations tested.

Comparative Example 7

Stability of Alternating Styrene/Maleic Acid Copolymer and Lipid Complexes at Physiological pH The ability of the alternating styrene/maleic acid copolymers and lipid of the prior art to form stable macromolecular complexes at physiological pH was investigated.

Method

A stock emulsion of lipid was prepared at double the desired final concentration. Lipid was added to the appropriate volume of water, followed by stirring and heating to approximately 50° C. until a uniform emulsion is formed. The emulsion was then homogenised for 10 minutes.

A stock solution of each polymer was prepared at double the desired final concentration. Polymers which were supplied as styrene/maleic anhydride were hydrolysed by refluxing in water for two hours in the presence of excess sodium hydroxide, before being left at 4° C. for 48 hours to ensure that the reaction was complete. Stock solutions were prepared by mixing of the hydrolysed polymer with the appropriate volume of water.

Polymer/lipid mixtures were then prepared by the dropwise addition of the lipid emulsion to an equal volume of polymer solution while stirring and heating to approximately 50° C.

The pH of the resulting mixtures was lowered using hydrochloric acid until the mixtures formed clear and colourless solutions (this pH value was then recorded). Subsequently the pH was carefully raised to approximately pH 7.0 using sodium hydroxide solution. Solutions were then stored at 4° C. for one hour prior to analysis.

Percentage values specified in this experiment refer to the weight of the component in question as a proportion of the total weight of the composition.

Mixtures were visually examined to determine whether the polymer component had solubilised the lipid component in the aqueous medium. The clarity of a mixture was categorised as being clear if there was no significant visible opacity to the naked eye, whereas a mixture was categorised as cloudy if there was significant visible disruption to the passage of light.

Polymers

The polymer referred to as Ald is available from Aldrich Chemical Company (USA), catalogue number 43,529-5. The polymer is a 1:1 alternating copolymer of styrene and maleic acid and is supplied as an aqueous concentrate.

SMA1000P was obtained from Sartomer Inc. and contains a 1:1 ratio of styrene to maleic anhydride monomer units. The polymer is supplied in powder form, as the unhydrolysed anhydride.

Lipid

Pro H was as described in Comparative Example 1.

Results

Table 7 below summarises the results of the experiment.

TABLE 7

Stability of alternating styrene/maleic acid copolymer and lipid complexes at physiological pH

| Polymer Component | Polymer Concentration % | Lipid Component | Lipid Concentration %† | Clarity | pH on clearing | Clarity at pH 7 |
|---|---|---|---|---|---|---|
| Ald | 2.5 | Pro H | 1 | Clear | 3.35 | No |
| SMA1000P* | 2.5 | Pro H | 1 | Clear | 3.4 | No |

*indicates that the polymer was hydrolysed before use
†Quantity of Pro H utilised is 5%, such that 1% lipid is present in the final preparation and 4% alcohol and glycerine.

Although these alternating styrene/maleic acid polymers solubilised the lipid mixture Pro H in the range pH 3.3-3.5, neither of the samples were stable when stored at physiological pH, precipitating out of solution within one hour of adjusting to pH 7.0. These findings highlight the issue of stability which exists with the polymer/lipid macromolecular complexes of the prior art.

EXAMPLES OF THE INVENTION

Example 1

The Use of Blocky Styrene/Maleic Acid Copolymers in the Formation of Polymer/Lipid Macromolecular Complexes An exemplary blocky styrene/maleic acid copolymer (i.e. hydrolysed blocky styrene/maleic anhydride copolymer) was tested and compared with examples of alternating styrene/maleic acid copolymers for their ability to solubilise pure lipids, indicating the formation of macromolecular polymer/lipid complexes.

Method

A stock emulsion of membrane forming lipid was prepared at double the desired final concentration. Lipid was added to the appropriate volume of water, followed by stirring and heating to approximately 50° C. until a uniform emulsion is formed. The emulsion was then homogenised for 10 minutes.

A stock solution of each polymer was prepared at double the desired final concentration. Polymers which were supplied as styrene/maleic anhydride were hydrolysed by refluxing in water for two hours in the presence of excess sodium hydroxide, before being left at 4° C. for 48 hours to ensure that the reaction was complete. Stock solutions were prepared by mixing of the hydrolysed polymer with the appropriate volume of water.

Polymer/lipid mixtures were then prepared by the dropwise addition of the lipid emulsion to an equal volume of polymer solution while stirring and heating to approximately 50° C.

The pH of the resulting mixtures were lowered to approximately pH 7, or for those mixtures which had not produced clear and colourless solutions at this point, it was further lowered until the solution cleared. Those mixtures which ultimately produced a clear and colourless solution after lowering of the pH to below 7 were subsequently raised in pH to observe whether they would remain clear when returned to physiological pH levels and left overnight at 4° C. Two items of information were noted, firstly whether a clear and colourless solution could be prepared, and secondly whether a stable clear and colourless solution could be prepared at physiological pH (i.e. approximately pH 7).

Percentage values specified in this experiment refer to the weight of the component in question as a proportion of the total weight of the composition.

Mixtures were visually examined to determine whether the polymer component had solubilised the lipid component in the aqueous medium. The clarity of a mixture was categorised as being clear if there was no significant visible opacity to the naked eye, whereas a mixture was categorised as cloudy if there was significant visible disruption to the passage of light.

Polymers

Ald was as described in Comparative Example 7.

SMA1000P was as described in Comparative Example 7.

SMA3000P was obtained from Sartomer Inc. and contains a 3:1 ratio of styrene to maleic anhydride monomer units (i.e. is a blocky copolymer). The polymer is supplied in powder form, as the unhydrolysed anhydride.

Lipids

DLPC (di-lauryl phosphatidyl choline), CAS Ref 18194-25-7, was obtained at 99% purity from Sigma-Aldrich.

DPPC (di-palmityl phosphatidyl choline), CAS Ref 63-89-8, was obtained at 99% purity from Sigma-Aldrich.

DPPG (di-palmityl phosphatidyl glycerol), CAS Ref 67232-81-9, was obtained as the sodium salt at 99% purity from Sigma-Aldrich.

Results

Table 8 below summarises the results of the experiment.

TABLE 8

The use of blocky and alternating styrene/maleic acid copolymers in the formation of polymer/lipid macromolecular complexes

| Polymer Component | Polymer Concentration % | Lipid Component | Lipid Concentration % | Clarity | Clarity at pH 7 |
| --- | --- | --- | --- | --- | --- |
| Ald | 2.5% | DLPC | 1% | Clear | No |
| Ald | 2.5% | DPPC | 1% | Clear | No |
| Ald | 2.5% | PG | 1% | Clear | No |
| SMA 1000P* | 2.5% | DLPC | 1% | Clear | No |
| SMA 1000P* | 2.5% | PG | 1% | Clear | No |
| SMA 3000P* | 2.5% | DLPC | 1% | Clear | Yes |
| SMA 3000P* | 2.5% | PG | 1% | Clear | Yes |

*indicates that the polymer was hydrolysed before use

A number of surprising conclusions may be made on the basis of the data in Table 8. Firstly, contrary to the expectation of one skilled in the art that a highly defined alternating structure is required for the interaction of an amphiphilic polymer and a membrane forming lipid, it has been demonstrated that blocky copolymers may interact in a similar way. Secondly, the selection of the precise monomer ratios in the blocky copolymer may enable the polymer/lipid interaction to occur stably at physiological pH.

Example 1

Supplemental

For a quantitative comparison of the performance of prior art mixtures compared to mixtures according to the present invention, representative samples were prepared according to the general procedure laid out in Example 1 (with the addition of cosurfactant) and examined using a turbidity meter (Nephla, from Hach-Lange). The turbidity meter was calibrated prior to use, with two known standards (0 and 40 FNU).

After the final stage of sample preparation (i.e. adjustment of the pH to physiological) samples were course filtered through Whatman 541 filter paper to remove any gross matter which could interfere with turbidity measurement. Immediately after filtration the first turbidity measurement was taken. Mixtures were stored at 4° C. following the initial measurement, and remeasured at later time points.

A full description of the components utilised in this supplemental experiment is available elsewhere in the Examples.

TABLE 8a

The use of blocky and alternating styrene/maleic acid copolymers in the formation of polymer/lipid macromolecular complexes

| Polymer Component | Lipid Component | Surfactant Component | Clearing pH | Turbidity at pH 7 (FNU) | | | | |
|---|---|---|---|---|---|---|---|---|
| | | | | 0 | 1 day | 2 days | 7 days | 14 days |
| Ald 2.5% | 90H 1.0% | F127 0.01% | ~3.5 | 174 | 202 | — | 411 | >1300 |
| SMA 1000P 2.5%* | 90H 1.0% | F127 0.01% | ~3.0 | 114 | 207 | 343 | 425 | 524 |
| SMA 2000P 2.5%* | 90H 1.0% | F127 0.01% | ~6.1 | 11 | — | — | — | 19 |
| SMA 3000P 2.5%* | 90H 1.0% | F127 0.01% | ~9.1 | 16 | — | — | — | 19 |

*indicates that the polymer was hydrolysed before use

The results of the supplemental experiments in Example 1 provide quantitative evidence that the compositions according to the present invention have improved stability at physiological pH (i.e. pH 7) when compared to compositions of the prior art.

Example 2

The Use of Blocky Styrene/Maleic Acid Copolymers and Natural Lipid Mixtures in the Formation of Polymer/Lipid Macromolecular Complexes In light of the results of Example 1, and the knowledge that blocky styrene/maleic acid polymers are capable of operating at physiological pH, the suitability of a range of natural lipid extracts for use in the present invention was tested. A number of commercially available lipid compositions, derived from egg or soy were analysed.

Method

A stock emulsion of membrane forming lipid was prepared at double (i.e. 2%) the desired final concentration of 1%. Lipid was added to the appropriate volume of water, followed by stirring and heating to approximately 50° C. until a uniform emulsion was formed. The emulsion was then homogenised for 10 minutes.

A stock solution of each polymer was prepared at double (i.e. 5%) the desired final concentration of 2.5%. Polymers which were supplied as styrene/maleic anhydride were hydrolysed by refluxing in water for two hours in the presence of excess sodium hydroxide, before being left at 4° C. for 48 hours to ensure that the reaction was complete. Stock solutions were prepared by mixing of the hydrolysed polymer with the appropriate volume of water.

Polymer/lipid mixtures were then prepared by the dropwise addition of the lipid emulsion to an equal volume of polymer solution while stirring and heating to approximately 50° C.

For those mixtures which did not immediately produce a clear and colourless solution, the pH of the mixture was lowered to determine whether a clear and colourless solution could possibly form at a lower pH level.

Percentage values specified in this experiment refer to the weight of the component in question as a proportion of the total weight of the composition.

Mixtures were visually examined to determine whether the polymer component had solubilised the lipid component in the aqueous medium. The clarity of a mixture was categorised as being clear if there was no significant visible opacity to the naked eye, whereas a mixture was categorised as cloudy if there was significant visible disruption to the passage of light.

Polymers

SMA2000P was obtained from Sartomer Inc. and contains a 2:1 ratio of styrene to maleic anhydride monomer units (i.e. is a blocky copolymer). The polymer is supplied in powder form, as the unhydrolysed anhydride.

SMA3000P was as described in Example 1.

Lipids

Epikuron 200 (Ep200) is a soy phosphatidyl choline of at least 92% purity. It is used as an emulsifier for pharmaceutical (including parenteral) applications and is known to form liposomes. Ep200 is available from Degussa Texturant Systems UK Ltd.

Epikuron 145V (Ep145V) is a de-oiled soy lecithin fraction enriched with phosphatidyl choline to at least 45% purity. Ep145V is available from Degussa Texturant Systems UK Ltd.

Emulmetik 970 (Em970) is a partially de-fatted egg lecithin containing at least 59% phosphatidyl cholines. It is used as a coemulsifier and forms liposomes. Em970 is available from Lucas Meyer Cosmetics SA.

Emulmetik 950 (Em950) is a purified, hydrogenated soy extract containing at least 94% phosphatidyl cholines. It is used as an emulsifier and forms liposomes. Em950 is available from Lucas Meyer Cosmetics SA.

Emulmetik 930 (Em930) was as described in Comparative Example 1.

Emulmetik 900 (Em900) is a de-oiled purified soy extract enriched with phosphatidyl choline to at least 45% purity. It is used as an emulsifier and forms liposomes. Em900 is available from Lucas Meyer Cosmetics SA.

Emulmetik 300 (Em300) is a de-oiled purified soy extract containing at least 97% phospholipids and glycolipids. It is used as a coemulsifier. Em300 is available from Lucas Meyer Cosmetics SA.

Epikuron 130P (Ep130P) is a de-oiled soy lecithin fraction enriched with phosphatidyl choline to at least 30% purity. It is used as an emulsifier, and is approved for pharmaceutical use. Ep130P is available from Degussa Texturant Systems UK Ltd.

Ovothin 120 (OVA120) is a natural mixture of egg lecithin and egg oils containing at least 22% phosphatidyl cholines. It has dietary uses, and is available from Degussa Texturant Systems UK Ltd.

Pro H was as described in Comparative Example 1.

Pro-Lipo Duo (Pro Duo) is a proliposomal composition, it is a liquid, containing a soy phospholipid content of approximately 50% with the remaining 50% made up from glycerol and alcohol. Pro Duo is available from Lucas Meyer Cosmetics SA.

Liposome 0041 (Lip0041) is a purified soy lecithin liposomal formulation, containing 10% phospholipids together with propylene glycol and water. Lip0041 is available from Lipoid GmbH.

S 75 is a purified soy extract containing 68-73% phosphatidyl choline. It is available from Lipoid GmbH.

S 100 is a purified soy extract containing at least 94% phosphatidyl choline. It is available from Lipoid GmbH.

S PC is a purified soy extract containing 98% phosphatidyl choline. It is available from Lipoid GmbH.

SL 80 is a purified soy extract containing 69% phosphatidyl choline. It is available from Lipoid GmbH.

SL 80-3 is a purified soy extract containing 54% phosphatidyl choline. It is available from Lipoid GmbH.

90H was as described in Comparative Example 1.

Phospholipon® 80H, referred to herein by the abbreviation 80H, available from Phospholipid GmbH (Germany), is a hydrogenated soy lecithin extract of at least 60% phosphatidyl choline content and is used as an emulsifier and forms liposomes. It is sold for use in cosmetics.

Phospholipon® 90 NG, referred to herein by the abbreviation 90NG, available from Phospholipid GmbH (Germany), is a soy lecithin extract of at least 90% phosphatidyl choline content. It is used as an emulsifier and forms liposomes, and is sold for use in pharmaceuticals and cosmetics.

Nat 8539 is a pre-formulated liposome composition, derived from soy extract, it contains 73-79% phosphatidyl choline, with the remainder as ethanol.

Results

Table 9 below summarises the results of the experiment and the composition of the lipid extract mixture on a dry weight basis (where available).

TABLE 9

The use of blocky styene/maleic acid copolymers and natural lipid mixtures in the formation of polymer/lipid macromolecular complexes

| Lipid Component | Natural Origin | Lipid Composition % | | | | | Clarity with hydrolysed SMA2000P | Clarity with hydrolysed SMA3000P |
| --- | --- | --- | --- | --- | --- | --- | --- | --- |
| | | PC | LPC | PE | Other PL | Free Fatty Acids | | |
| Ep200 | SOY | >92 | <3 | UNKNOWN | <2 | UNKNOWN | Clear | Clear |
| Ep145V | SOY | >45 | <4 | >10 | PI < 3 | UNKNOWN | Cloudy | Cloudy |
| Em970 | EGG | >59 | UNKNOWN | >6 | PLR > 5 | UNKNOWN | Cloudy | Cloudy |
| Em950† | SOY | >94 | <1 | UNKNOWN | <3 | UNKNOWN | Clear | Clear |
| Em930 | SOY | >92 | <3 | UNKNOWN | <2 | UNKNOWN | Clear | Clear |
| Em900 | SOY | >45 | UNKNOWN | <10 | PA < 3.0 | UNKNOWN | Cloudy | Cloudy |
| Em300 | SOY | | | | PL + GL > 97 | | Cloudy | Cloudy |
| Ep130P | SOY | 30-33 | UNKNOWN | 16-19 | PI 9-12 | UNKNOWN | Cloudy | Cloudy |
| OVA120 | EGG | >22 | <1 | >6 | <3 | ARA 1.8-2.5, DHA 0.8-1.4 | Cloudy | Cloudy |
| Pro H*~ | SOY | | | | UNKNOWN | | Clear | Clear |
| Pro DUO* | SOY | | | | UNKNOWN | | Clear | Clear |
| Lip 0041* | SOY | | | | UNKNOWN | | Clear | Clear |
| S 75‡ | SOY | 68-73 | <3.0 | 7-10 | | UNKNOWN | Clear | Clear |
| S 100 | SOY | >94 | <3.0 | <0.1 | PI < 0.1 | NON-PLR < 3.0 | Clear | Clear |
| S PC | SOY | 98 | 0.20 | <0.1 | <0.1 | <0.05 | Clear | Clear |
| SL 80 | SOY | 69 | 15.60 | | UNKNOWN | | Clear | Clear |
| SL 80-3 | SOY | 54 | 21.70 | | UNKNOWN | | Clear | Clear |
| 90H† | SOY | >90 | <4.0 | | UNKNOWN | | Clear | Clear |
| 80H† | SOY | >60 | <10 | | UNKNOWN | | Clear | Clear |
| 90NG | SOY | >90% | <6.0 | | UNKNOWN | | Clear | Clear |
| Nat 8539* | SOY | | | | UNKNOWN | | Clear | Clear |

Key:
PC = phosphatidyl choline
LPC = lyso-phosphatidyl choline
PE = phosphatidyl ethanolamine
PI = phosphatidyl inositol
PL = phospholipid
PA = phosphatidic acid
GL = glycolipid
ARA = arachidonic acid
DHA = docosahexaenoic acid
PLR = polar lipid
* = pre-formed liposomal formulation
† = hydrogenated
‡ = Not completely clear
~ = Quantity of Pro H utilised is 5%, such that 1% lipid is present in the final preparation and 4% alcohol and glycerine.

Example 2 demonstrates that two exemplary blocky styrene/maleic acid copolymers are capable of solubilising a broad range of membrane forming lipid mixtures derived from natural sources. This finding is of some significance, since the polymer/lipid systems of the prior art exemplify only the use of highly pure synthetic lipids in isolation or, in one example only, as a two component mixture. The lipid extracts shown above are extremely complex natural products whose contents vary both in the nature of the phospholipid headgroups present and in their associated acyl chains (chain length and degree of unsaturation). The experiment therefore demonstrates the versatility of the polymers of the present invention in solubilising a broad range of membrane forming lipid mixtures to form substantially clear and colourless aqueous solutions.

Example 2

Supplemental

For a quantitative demonstration of the clarity and stability of mixtures according to the present invention when prepared with different lipid mixtures, samples were prepared according to the general procedure laid out in Example 2 and examined using a turbidity meter (Nephla, from Hach-Lange). The turbidity meter was calibrated prior to use, with two known standards (0 and 40 FNU).

After the final stage of sample preparation (i.e. adjustment of the pH to physiological) samples were course filtered through Whatman 541 filter paper to remove any gross matter which could interfere with turbidity measurement. Immediately after filtration the first turbidity measurement was taken. Mixtures were stored at 4° C. following the initial measurement, and remeasured at later time points.

Results for these experiments are shown in Table 9a below.

The results in Table 9a are generally in agreement with those in Table 9 above, although a number of minor discrepancies exist. These discrepancies may be explained as a result of the subjective nature of the earlier results and the fact that clarity is defined in Table 9 by only two categories (clear or cloudy). Experimental variation and batch to batch changes in lipids (which are natural extracts and therefore subject to some variation) may also contribute.

In summary, it is clear that the compositions of the present invention prepared using a range of lipid components may attain higher levels of clarity and/or may be more stable than corresponding compositions of the prior art.

Example 3

The Use of a Range of Blocky Styrene/Maleic Acid Copolymers and Lipid in the Formation of Polymer/Lipid Macromolecular Complexes To confirm the surprising finding that blocky styrene/maleic acid copolymers are suitable for use in the formation of polymer/lipid macromolecular complexes, and that this applies to a broad range of monomer ratios, examples of a number of different commercially available polymers were tested.

Method

A stock emulsion of membrane forming lipid was prepared at double (i.e. 2%) the desired final concentration of 1%. Lipid was added to the appropriate volume of water, followed by stirring and heating to approximately 50° C. until a uniform emulsion was formed. The emulsion was then homogenised for 10 minutes.

A stock solution of each polymer was prepared at double (i.e. 5%) the desired final concentration of 2.5%. Polymers which were supplied as styrene/maleic anhydride were hydrolysed by refluxing in water for two hours in the presence of excess sodium hydroxide, before being left at 4° C. for 48 hours to ensure that the reaction was complete. Stock solutions were prepared by mixing of the hydrolysed polymer with the appropriate volume of water.

Polymer/lipid mixtures were then prepared by the dropwise addition of the lipid emulsion to an equal volume of polymer solution while stirring and heating to approximately 50° C.

The pH of the mixtures was adjusted to determine the critical level at which macromolecular assemblies formed, and whether the resulting clear and colourless solution would remain at physiological pH.

Percentage values specified in this experiment refer to the weight of the component in question as a proportion of the total weight of the composition.

Mixtures were visually examined to determine whether the polymer component had solubilised the lipid component in TABLE 9a The use of blocky styene/maleic acid copolymers and natural lipid mixtures in the formation of polymer/lipid macromolecular complexes

| Lipid Component | Clarity (FNU) with hydrolysed SMA2000P | | | | | Clarity (FNU) with hydrolysed SMA3000P | | | | |
|---|---|---|---|---|---|---|---|---|---|---|
| | 0 | 2 weeks | 4 weeks | 8 weeks | 16 weeks | 0 | 2 weeks | 4 weeks | 8 weeks | 16 weeks |
| Ep200 | 12 | 9 | 12 | 7 | 6 | 33 | 66 | 72 | 72 | 75 |
| Ep145V | 47 | 52 | 49 | 49 | 123 | 141 | >1300 | >1300 | >1300 | >1300 |
| Em970 | 171 | >1300 | >1300 | >1300 | >1300 | 281 | >1300 | >1300 | >1300 | >1300 |
| Em950 | 1194 | >1300 | >1300 | >1300 | >1300 | 62 | 101 | 128 | 281 | >1300 |
| Em930 | 13 | 9 | 8 | 6 | 6 | 31 | 48 | 51 | 50 | 45 |
| Em900 | 115 | >1300 | >1300 | >1300 | >1300 | 69 | 84 | 127 | 170 | 3 |
| Em300 | 60 | 44 | 40 | 67 | 163 | 34 | 57 | 74 | 119 | 142 |
| Ep130P | 85 | 78 | 152 | 159 | 462 | 98 | 128 | 110 | 123 | 343 |
| OVA120 | 332 | >1300 | >1300 | >1300 | >1300 | 499 | >1300 | >1300 | >1300 | >1300 |
| Pro H | 60 | 62 | 76 | 78 | 62 | 4 | 5 | 6 | 12 | 30 |
| Pro DUO | 32 | 31 | 26 | 18 | 14 | 60 | 74 | 76 | 66 | 78 |
| Lip 0041 | 9 | 9 | 9 | 5 | 4 | 37 | 44 | 51 | 51 | 67 |
| S 75 | 3 | 3 | 3 | 2 | 3 | 80 | 107 | 111 | 122 | 134 |
| S 100 | 5 | 4 | 4 | 3 | 4 | 34 | 53 | 66 | 58 | 70 |
| S PC | 4 | 4 | 3 | 4 | 17 | 19 | 34 | 45 | 48 | 51 |
| SL 80 | 5 | 5 | 11 | 36 | 157 | 16 | 31 | 33 | 49 | 165 |
| SL 80-3 | 12 | 23 | 41 | 45 | 47 | 14 | 18 | 31 | 111 | 324 |
| 90H† | 11 | 19 | 14 | 17 | 15 | 16 | 19 | 19 | 18 | 18 |
| 80H† | 38 | 41 | 54 | 37 | 48 | 15 | 27 | 42 | 62 | 39 |
| 90NG | 11 | 8 | 7 | 6 | 6 | 27 | 41 | 51 | 54 | 67 |
| Nat 8539 | 6 | 6 | 19 | 26 | 32 | 50 | 71 | 76 | 76 | 114 | the aqueous medium. The clarity of a mixture was categorised as being clear if there was no significant visible opacity to the naked eye, whereas a mixture was categorised as cloudy if there was significant visible disruption to the passage of light.
Polymers
   SMA2000P was as described in Example 2.
   SMA3000P was as described in Example 1.
   SMA3000HNa was as described in Comparative Example 4.
   SMA4000HNa was obtained from Sartomer Inc. and contains a 4:1 ratio of styrene to maleic acid monomer units (i.e. is a blocky copolymer). The polymer is supplied in a hydrolysed sodium salt form, as a resin.
Lipids
   Em930 was as described in Comparative Example 1.
Results
   Table 10 below summarises the results of the experiment.

TABLE 10

The use of a range of blocky styrene/maleic acid copolymers and lipid in the formation of polymer/lipid macromolecular complexes

| Polymer Component | Polymer Concentration % | Lipid Component | Lipid Concentration % | Clarity | pH on clearing | Clarity at pH 7 |
|---|---|---|---|---|---|---|
| SMA2000P* | 2.5 | Em930 | 1.0 | Clear | 8.68 | Yes |
| SMA3000P* | 2.5 | Em930 | 1.0 | Clear | 8.95 | Yes |
| SMA3000HNa | 2.5 | Em930 | 1.0 | Clear | 8.96 | Yes |
| SMA4000HNa | 2.5 | Em930 | 1.0 | Clear | 11.65 | No |

*indicates the polymer was hydrolysed before use

The data in Table 10 indicate that SMA2000, SMA3000 (each being in hydrolysed form) and SMA3000HNa are capable of producing clear and colourless aqueous solutions when combined with an exemplary lipid Em930, and the solutions are stable at pH 7. SMA4000HNa does not solubilise Em930 at pH 7 as the polymer precipitates out of solution, though it is capable of solubilising Em930 at pH levels above this point.

Example 3

Supplemental

For a quantitative comparison of the performance of mixtures according to the present invention with a range of styrene to maleic acid ratios at physiological pH, representative samples were prepared according to the general procedure laid out in Example 3 and examined using a turbidity meter (Nephla, from Hach-Lange). The turbidity meter was calibrated prior to use, with two known standards (0 and 40 FNU).

After the final stage of sample preparation (i.e. adjustment of the pH to physiological) samples were course filtered through Whatman 541 filter paper to remove any gross matter which could interfere with turbidity measurement. Immediately after filtration the first turbidity measurement was taken. Mixtures were stored at 4° C. following the initial measurement, and remeasured at later time points.

A full description of the components utilised in this supplemental experiment is available elsewhere in the Examples.

TABLE 10a

The use of blocky and alternating styrene/maleic acid copolymers in the formation of polymer/lipid macromolecular complexes

| Polymer Component | Lipid Component | Clearing pH | Turbidity at pH 7 (FNU) | | | | |
|---|---|---|---|---|---|---|---|
| | | | 0 | 2 weeks | 4 weeks | 8 weeks | 16 weeks |
| SMA 2000P 2.5%* | Em930 1.0% | ~5.7 | 13 | 9 | 8 | 6 | 6 |
| SMA 3000P 2.5%* | Em930 1.0% | ~8.1 | 31 | 48 | 51 | 50 | 45 |
| SMA4000HNa 2.5% | Em930 1.0% | ~9.0 | 1090 | >1300 | >1300 | >1300 | >1300 |

*indicates that the polymer was hydrolysed before use

The results of the supplemental experiments in Example 3 provide quantitative evidence that copolymer with styrene to maleic acid ratios of 2:1 or 3:1 are both able to produce stable macromolecular assemblies at physiological pH (i.e. pH 7).

Example 4

The Use of a Cosurfactant in Compositions of the Invention

As demonstrated above, blocky styrene/maleic acid copolymers are capable of interacting with a range of lipids to form macromolecular polymer/lipid complexes. Although there was no significant level of disruption to the passage of light in the examples shown, however, the addition of a cosurfactant was tested as a means of ensuring that solutions were completely clear, with no disruption to the passage of light.

component in the aqueous medium. The clarity of a mixture was categorised as being clear if there was no significant visible opacity to the naked eye, whereas a mixture was categorised as cloudy if there was significant visible disruption to the passage of light.

Polymers

SMA3000HNa was as described in Comparative Example 4.

SMA4000HNa was as described in Example 3.

Lipid

Em930 was as described in Comparative Example 1.

Surfactants

F127 and S LPC were as described in Comparative Example 1.

Results

Table 11 below summarises the results of the experiment.

TABLE 11

| The use of a cosurfactant in compositions of the invention | | | | | | | |
|---|---|---|---|---|---|---|---|
| Polymer | Polymer Concentration % | Lipid | Lipid Concentration % | Surfactant | Surfactant Concentration % | Clarity | pH on clearing | Clarity at pH 7 |
| SMA2000P* | 2.5 | Em930 | 1.0 | S LPC | 0.01 | Clear | 8.68 | Clear |
| SMA3000P* | 2.5 | Em930 | 1.0 | S LPC | 0.01 | Clear | 8.95 | Clear |
| SMA2000P* | 2.5 | Em930 | 1.0 | F127 | 0.01 | Clear | 8.72 | Clear |
| SMA3000P* | 2.5 | Em930 | 1.0 | F127 | 0.01 | Clear | 8.91 | Clear |

*indicates the polymer was hydrolysed before use

Method

A stock emulsion of cosurfactant and membrane forming lipid was prepared at double the desired final concentration. Cosurfactant was dissolved in water while heating (approximately 50° C.) and stirring. Lipid was then added, followed by continued stirring and heating until a uniform emulsion is formed. The emulsion was then homogenised for 10 minutes.

A stock solution of each polymer was prepared at double (i.e. 5%) the desired final concentration of 2.5%. Polymers which were supplied as styrene/maleic anhydride were hydrolysed by refluxing in water for two hours in the presence of excess sodium hydroxide, before being left at 4° C. for 48 hours to ensure that the reaction was complete. Stock solutions were prepared by mixing of the hydrolysed polymer with the appropriate volume of water.

Polymer/lipid mixtures were then prepared by the dropwise addition of the lipid containing emulsion to an equal volume of polymer solution while stirring and heating to approximately 50° C.

The pH of the mixtures was adjusted to determine the critical pH level at which macromolecular assemblies formed, and whether the resulting clear and colourless solution would remain at physiological pH.

Percentage values specified in this experiment refer to the weight of the component in question as a proportion of the total weight of the composition.

Mixtures were visually examined to determine whether the polymer and surfactant components had solubilised the lipid The use of a small quantity of cosurfactant (equivalent to only 1% of the lipid component) does not disrupt the ability of the compositions to form clear and colourless solutions which are stable at pH 7. On the contrary, even a small amount of cosurfactant contributed to the clarity to provide solutions that were 'water' clear.

Example 4

Supplemental

For a quantitative comparison of the performance of mixtures according to the present invention which contain cosurfactant with mixtures which are absent of cosurfactant, representative samples were prepared according to the general procedure laid out in Example 4 and examined using a turbidity meter (Nephla, from Hach-Lange). The turbidity meter was calibrated prior to use, with two known standards (0 and 40 FNU).

After the final stage of sample preparation (i.e. adjustment of the pH to physiological) samples were course filtered through Whatman 541 filter paper to remove any gross matter which could interfere with turbidity measurement. Immediately after filtration the first turbidity measurement was taken. Mixtures were stored at 4° C. following the initial measurement, and remeasured at later time points.

A full description of the components utilised in this supplemental experiment is available elsewhere in the Examples.

TABLE 11a

The use of blocky and alternating styrene/maleic acid copolymers in the formation of polymer/lipid macromolecular complexes

| Polymer Component | Lipid Component | Surfactant Component | Clearing pH | Turbidity at pH 7 (FNU) | | | | |
|---|---|---|---|---|---|---|---|---|
| | | | | 0 | 2 weeks | 4 weeks | 8 weeks | 16 weeks |
| SMA 2000P 2.5%* | Em930 1.0% | — | ~5.7 | 13 | 9 | 8 | 6 | 6 |
| SMA 3000P 2.5%* | Em930 1.0% | — | ~8.1 | 31 | 48 | 51 | 50 | 45 |
| SMA 2000P 2.5%* | Em930 1.0% | F127 0.01% | ~6.2 | 5 | 4 | 4 | 4 | 4 |
| SMA 3000P 2.5%* | Em930 1.0% | F127 0.01% | ~9.1 | 19 | 13 | 19 | 12 | 10 |

*indicates that the polymer was hydrolysed before use

The results of the supplemental experiments in Example 4 provide quantitative evidence that a small quantity of cosurfactant may aid the clarity of compositions of the present invention.

Example 5

The Use of Compositions of the Invention to Solubilise Exemplary Active Agents

As demonstrated above, blocky styrene/maleic acid copolymers are capable of interacting with a range of lipids to form macromolecular polymer/lipid complexes. Such polymer/lipid complexes may be expected to be of use in the solubilisation of active agents which have a poor aqueous solubility. Compositions according to the present invention were therefore tested with a range of exemplary active agents with poor aqueous solubility to illustrate the potential application of the compositions in the fields of cosmetics and pharmaceuticals.

Method

A stock emulsion of cosurfactant, membrane forming lipid and active was prepared at double the desired final concentration. Cosurfactant was dissolved in water while heating (approximately 50° C.) and stirring. Lipid was then added, followed by continued stirring and heating until a uniform emulsion is formed. The emulsion was then homogenised for 10 minutes. After re-heating to approximately 50° C. the active component was added slowly under stirring until a uniform emulsion was present. The final emulsion was then homogenised for a further 10 minutes.

A stock solution of each polymer was prepared at double (i.e. 5%) the desired final concentration of 2.5%. Polymers which were supplied as styrene/maleic anhydride were hydrolysed by refluxing in water for two hours in the presence of excess sodium hydroxide, before being left at 4° C. for 48 hours to ensure that the reaction was complete. Stock solutions were prepared by mixing of the hydrolysed polymer with the appropriate volume of water.

Polymer/lipid mixtures were then prepared by the drop-wise addition of the lipid containing emulsion to an equal volume of polymer solution while stirring and heating to approximately 50° C.

The pH of the mixtures was adjusted to determine the critical pH level at which macromolecular assemblies formed, and whether the resulting clear and colourless solution would remain at physiological pH.

Percentage values specified in this experiment refer to the weight of the component in question as a proportion of the total weight of the composition.

Mixtures were visually examined to determine whether the polymer/lipid assemblies had solubilised the active agent in the aqueous medium. The clarity of a mixture was categorised as being clear if there was no significant visible opacity to the naked eye, whereas a mixture was categorised as cloudy if there was significant visible disruption to the passage of light.

Furthermore, certain of the examples were freeze-dried and then reconstituted into water (with stirring and warming) to determine whether the macromolecular assemblies remained stable under these handling conditions. After reconstitution solutions were again examined for clarity.

Polymers

SMA3000HNa was as described in Comparative Example 4.

SMA2000P was as described in Example 3.

SMA3000P was as described in Example 1.

Lipids

The lipids 90H, Pro H and Em930 were as described in Comparative Example 1.

Surfactants

F127 and S LPC were as described in Comparative Example 1.

Active Agents

TECA was as described in Comparative Example 2.

Argireline® (Argir), also known as acetyl hexapeptide 3, is available from Lipotec SA (Spain).

L-ascorbyl palmitate (Asc-P), is a vitamin C monopalmitate derivative, CAS Ref 137-66-6. It is available from DSM (Switzerland).

Nikkol CP(CP), is a vitamin C dipalmitate derivative, CAS Ref 28474-90-0. CP is available from Nikko Chemicals Co Ltd (Japan).

Nikkol VC-IP (VC-IP), is a vitamin C tetraisopalmitate derivative, CAS Ref 183476-82-6. VC-IP is available from Nikko Chemicals Co Ltd (Japan).

Asiaticoside (Asi) is a glycosidic derivative of asiatic acid. It was utilised at 95% purity, and is available from Roche Nicholas Laboratories SA—Serdex Division (France), now Bayer Sante Familiale.

β-carotene (β-Car) is a pro-vitamin A, supplied as 30% FS grade (as an oil) by DSM Nutritional Products Ltd. CAS Ref 7235-40-7.

Ceramide IIIA (Cera) was supplied by Degussa/Goldschmidt AG (Germany). Cholesterol (Chol), CAS Ref 57-88-5, was used at >95% BP/Ph Eur grade. Chol is available from Merck KGaA.

Matrixyl™ (Mat) is palmityl-KTTKS. It was utilised as a gel, containing 120 ppm of the peptide, and is available from Sederma SAS (France).

Retinol palmitate (Ret-P), is vitamin A palmitate, CAS Ref 79-81-2. Ret-P was supplied by DSM (Switzerland) at 1.7 million IU per gram.

Results

Table 12 below summarises the results of the experiment.

TABLE 12

The ability of compositions of the invention to solubilise active agents

| Polymer | Polymer % | Lipid | Lipid % | Surfactant | Surfactant % | Active Agent | Active Agent % | Clarity | pH on clearing | Clarity at pH 7 | Freeze Drying |
|---|---|---|---|---|---|---|---|---|---|---|---|
| SMA 3000HNa | 2.5% | 90H | 1% | F127 | 0.01% | TECA | 0.1% | Clear | 8.92 | Clear | — |
| SMA 3000HNa | 2.5% | 90H | 1% | F127 | 0.01% | TECA | 0.4% | Clear | 8.92 | Clear | — |
| SMA 3000HNa | 2.5% | 90H | 1% | F127 | 0.01% | TECA | 0.8% | Clear | 8.95 | Clear | — |
| SMA 3000HNa | 2.5% | 90H | 1% | F127 | 0.01% | TECA | 0.1% | Clear | 8.92 | Clear | Yes |
| SMA 3000HNa | 2.5% | 90H | 1% | F127 | 0.01% | TECA | 0.4% | Clear | 8.92 | Clear | Yes |
| SMA 3000HNa | 2.5% | 90H | 1% | F127 | 0.01% | TECA | 0.8% | Clear | 8.95 | Clear | Yes |
| SMA 3000P*† | 2.5% | 90H | 1% | F127 | 0.01% | TECA | 0.8% | Clear | 8.86 | Clear | Yes |
| SMA 2000P* | 2.5% | 90H | 1% | F127 | 0.01% | TECA | 0.8% | Clear | 8.86 | Clear | Yes |
| SMA 3000P* | 2.5% | 90H | 1% | S LPC | 0.01% | TECA | 0.8% | Clear | 8.86 | Clear | Yes |
| SMA 2000P* | 2.5% | 90H | 1% | S LPC | 0.01% | TECA | 0.8% | Clear | 8.89 | Clear | Yes |
| SMA 3000HNa | 2.5% | 90H | 1% | F127 | 0.01% | Asi | 0.1% | Clear | 8.92 | Clear | — |
| SMA 3000HNa | 2.5% | 90H | 1% | F127 | 0.01% | Asi | 0.4% | Clear | 8.92 | Clear | — |
| SMA 3000HNa | 2.5% | 90H | 1% | F127 | 0.01% | Asi | 0.8% | Clear | 8.95 | Clear | — |
| SMA 3000HNa | 2.5% | 90H | 1% | F127 | 0.01% | Asi | 0.8% | Clear | 8.95 | Clear | Yes |
| SMA 3000P* | 2.5% | 90H | 1% | F127 | 0.01% | Asi | 0.8% | Clear | 8.95 | Clear | Yes |
| SMA 2000P* | 2.5% | 90H | 1% | F127 | 0.01% | Asi | 0.8% | Clear | 8.86 | Clear | Yes |
| SMA 3000HNa | 2.5% | 90H | 1% | S LPC | 0.01% | Asi | 0.8% | Clear | 8.95 | Clear | Yes |
| SMA 3000HNa | 1.50% | 90H | 1% | S LPC | 0.01% | Asi | 0.6% | Clear | 8.95 | Clear | — |
| SMA 3000HNa | 2.5% | 90H | 1% | S LPC | 0.01% | VC-IP | 0.1% | Clear | 8.89 | Clear | — |
| SMA 3000HNa | 2.5% | 90H | 1% | S LPC | 0.01% | CP | 0.1% | Clear | 8.89 | Clear | — |
| SMA 3000HNa | 2.5% | 90H | 1% | S LPC | 0.01% | Ret-P | 0.25% | Clear | 8.95 | Clear | — |
| SMA 3000HNa | 2.5% | 90H | 1% | S LPC | 0.01% | β-Car | 0.10% | Clear | 8.83 | Clear | — |
| SMA 3000HNa | 2.5% | 90H | 1% | S LPC | 0.01% | β-Car | 0.25% | Clear | 8.83 | Clear | — |
| SMA 3000HNa | 2.5% | 90H | 1% | S LPC | 0.01% | Asc-P | 0.1% | Clear | 8.87 | Clear | — |
| SMA 3000HNa | 2.5% | 90H | 1% | S LPC | 0.01% | Chol | 0.1% | Clear | 8.95 | Clear | — |
| SMA 3000HNa | 2.5% | 90H | 1% | S LPC | 0.01% | Mat | 0.5% | Clear | 8.86 | Clear | — |
| SMA 3000HNa | 2.5% | 90H | 1% | S LPC | 0.01% | Argir | 0.3% | Clear | 8.84 | Clear | — |
| SMA 3000HNa | 2.5% | 90H | 1% | S LPC | 0.01% | Cera | 0.1% | Clear | 8.89 | Clear | — |
| SMA 3000HNa | 2.5% | Em930 | 1% | S LPC | 0.01% | TECA | 0.5% | Clear | — | Clear | — |
| SMA 3000HNa | 2.5% | Pro H | 1% | S LPC | 0.01% | TECA | 0.5% | Clear | — | Clear | — |

— indicates not tested

*indicates the polymer was hydrolysed before use

†sample used for reconstitution test of freeze-dried material

Compositions of the present invention, based on a range of polymers or lipid components, demonstrate a potent ability to solubilise active agents with a known poor water solubility to form clear and colourless aqueous solutions which are stable at physiological pH. For example, the exemplary active agent TECA was solubilised at 0.8%, equivalent to approximately 18.5% of the total dry weight (80% of lipid weight). Comparative Example 2 indicated that none of the four common surfactants SDS, Mackanate, F127, S LPC were capable of solubilising TECA at 9.1% of total dry weight, irrespective of any other potential problems these surfactants may have.

At this time, concentrations of actives higher than those listed above have not been tested. Therefore the possibility exists that some of the active agents may be solubilised by the compositions of the invention at higher levels than those indicated.

Of those samples which were freeze-dried, all were easily reconstituted into water at the same concentration as prior to freeze-drying. This stability on processing is of value in commercial applications, where the transfer of freeze-dried formulations may significantly reduce transportation and handling costs.

Reconstitution of the freeze-dried composition containing SMA3000P (in hydrolysed form), 90H, F127 and TECA (indicate in Table 12 by t) was successful at a concentration of 30% total weight (i.e. an overall 5.5% concentration of active in the final aqueous solution). This finding indicates that formulations of varying concentration may be prepared from a single freeze-dried stock.

Example 5

Supplemental

For a quantitative demonstration of the performance of compositions of the invention as solubilising agents for a range of exemplary active agents with poor aqueous solubility, representative samples were prepared according to the general procedure laid out in Example 5 and examined using a turbidity meter (Nephla, from Hach-Lange). The turbidity meter was calibrated prior to use, with two known standards (0 and 40 FNU).

After the final stage of sample preparation (i.e. adjustment of the pH to physiological) samples were course filtered through Whatman 541 filter paper to remove any gross matter which could interfere with turbidity measurement. Immediately after filtration the first turbidity measurement was taken. Mixtures were stored at 4° C. following the initial measurement, and remeasured at later time points.

A full description of many of the components utilised in this supplemental experiment is available elsewhere in the Examples. Other active agents include:

Hydrocortisone (HC) Ph. Eur./USP/JP grade supplied by Sanofi Aventis Pharma SA. (France). CAS 50-23-7.

Clobetasol Propionate Micronized (Clo. P) BP/USP grade supplied by Farmabios S.p.A. (Italy). CAS 25122-46-7.

Dexamethasone (DEX) Ph. Eur./USP/JP supplied by Sanofi Aventis Pharma SA. (France). CAS 50-02-2.

Clobetasone Butyrate (Clo. But.) supplied by Sigma-Aldrich (UK). CAS 25122-57-0.

Hydrocortisone Butyrate (HC But.) Hydrocortisone 17-butyrate, supplied by Sigma-Aldrich (UK). CAS13609-67-1.

Dexamethasone Acetate Anhydrous (DEX A.A.) Ph. Eur./USP grade supplied by Sanofi Aventis Pharma SA. (France).

Cortisone Acetate Micronised (Cort. A.) Ph. Eur./USP/JP grade supplied by Sanofi Aventis Pharma SA. (France).

Hydrocortisone Acetate Micronised (HC A) Ph. Eur./USP/JP grade supplied by Sanofi Aventis Pharma SA. (France).

Eusolex 2292 (Octyl methoxycinimate) supplied by Rona, Merck KGaA. (Germany). CAS 5466-77-3.

Eusolex 4360 (Benzophenone-3) supplied by Merck KGaA. (Germany). CAS131-57-7.

Soy Isoflavones 50% CG (Soy Iso.) extract of Glycine Soja supplied by Sabinsa Corp. (U.S.A).

Rosmarinic Acid 90% (Ros. Acid) extract of *Melissa officinalis* supplied by Sabinsa Corp. (U.S.A). CAS 84604-14-8.

Licorice CG, extract of *Glycyrrhiza glabra* supplied by Sabinsa Corp. (U.S.A). CAS 84775-66-6.

Green Tea CG extract of *Camellia sinensis* (Epigallocatechin) supplied by Sabinsa Corp. (U.S.A). CAS 84650-60-2.

Minoxidil supplied by Flamma S.p.A. (Italy). CAS 38304-91-5.

Erythromycin Sulphate (Erythro.) supplied by SM Biomed Sdn. Bhd. (Malaysia) CAS114-07-8.

Neomycin Sulphate (Neo. Sulphate) supplied by Leshan Sanjiu-LongMarch Pharmarceuticals Co., Ltd. (China). CAS1405-10-3.

Ketaconazole (Keta.) Ph. Eur grade supplied by Nicholas Piramal India Limited. (India). CAS 65277-42-1.

PABA (4-Aminobenzoic acid extra pure) USP supplied by Merck KGaA. (Germany). CAS150-13-0.

Boswellin® CG extract of Boswellia serrata (β-boswellic acids) supplied by Sabinsa Corp. (U.S.A). CAS 97952-72-2.

Cholesterol Potassium Sulphate (Chol. Sulphate) supplied by MMP Inc. (U.S.A). CAS 6614-96-6.

7-Dehydrocholesterol (7-DHC), Provitamin $D_3$, supplied by MMP Inc. (U.S.A). CAS 000434-16-2.

Melaleucole (Melal.) Terpinen-4-ol supplied by SNP Natural products Pty Ltd. (Australia). CAS 562-74-3.

Galanga extract of *Kaempferia galanga* (Ethyl-p-methoxycinnamate 98%) supplied by Sabinsa Corp. (U.S.A). CAS 99880-64-5

Cosmoperine® (Cosm.) extract of *Piper nigrum* (Tetrahydropiperine) supplied by Sabinsa Corp. (U.S.A).

P-U. (Polyol soluble liquorice extract) extract of *Glycyrrhiza inflata* supplied by Maruzen Pharmaceuticals Co. Ltd. (Japan).

PT-40 (Polyol soluble liquorice extract P-T(40)) extract of *Glycyrrhiza glabra* supplied by Maruzen Pharmaceuticals Co. Ltd. (Japan). CAS 84775-66-6.

Ceramide IIIB (Cera. IIIB) supplied by Degussa Care Specialities. Cosmoferm B.V. (Netherlands).

Nystatin BP/Eur. Ph. grade supplied by Antibiotice S.A. (Romania) CAS1400-61-9.

Unisol S-22 (3-Benzylidene camphor) supplied by Induchem (Switzerland). CAS15087-24-8.

Avobenzene supplied by Unifect (UK). CAS 70356-09-1.

Clotrimazole (Clot.) USP/Ph. Eur. grade supplied by Farchemia S.R.L. (Italy). CAS 23593-75-1.

Ceramide H03 (Cera. H03) supplied by Sederma S.A.S. (France) CAS131276-37-4

Questice CQ U/A (Menthyl PCA) supplied by Quest International (UK).

CAS 68127-22-0.

Unisex Bouquet (AFL-3607/A) supplied by Arriva Fragrances (UK).

Apricosal (AFL-3607/E) supplied by Arriva Fragrances (UK).

Fougere (AFL-3607/D) supplied by Arriva Fragrances (UK).

Peppermint Oil (Pep-mint Oil) (AFL-3607/C) supplied by Arriva Fragrances (UK).

NDGA (Nordihydroguaiaretic acid) supplied by Whyte Chemicals Ltd. (UK). CAS 500-38-9.

Vitamin $D_3$ (Cholecalciferol) Ph. Eur/BP/USP supplied by Merck KGaA. (Germany). CAS 67-97-0.

Caffeine laboratory reagent grade supplied by Breckland Scientific Supplies (UK). CAS 58-08-2.

Herbalia Nettle extract of *Urtica dioica* supplied by Cognis Iberia s.l. (Spain).

Horse Chestnut extract of *Aesculus hippocastanum* supplied by Cognis Iberia s.l. (Spain).

Ginkgo (Herbalia Ginkgo CG) extract of *Ginkgo biloba* supplied by Cognis Iberia s.l. (Spain).

GSF (*Ginkgo Biloba* Extract G320) extract of *Ginkgo biloba* supplied by Linnea SA (Switzerland).

G38 (*Ginkgo Biloba* Extract G328) extract of *Ginkgo biloba* supplied by Linnea SA (Switzerland).

Octopirox (Piroctone olamine) supplied by Clariant UK Ltd. (UK), CAS 68890-66-4.

Results

Table 12a below summarises the results of the experiment.

TABLE 12a

The ability of compositions of the invention to solubilise active agents

| Polymer | Polymer % | Lipid | Lipid % | Surfactant | Surfactant % | Active Agent | Active Agent % | Clarity | pH on clearing | Turbidity at pH 7 (FNU) |
|---|---|---|---|---|---|---|---|---|---|---|
| SMA 3000P* | 2.5% | 90H | 1% | S LPC | 0.01% | HC | 0.25% | Clear | 8.97 | 9.09 |
| SMA 3000P* | 2.5% | 90H | 1% | S LPC | 0.01% | Clo. P | 0.1% | Clear | 8.85 | 50 |
| SMA 3000P* | 2.5% | 90H | 1% | S LPC | 0.01% | DEX | 0.25% | Clear | 8.82 | 58.6 |
| SMA 3000P* | 2.5% | 90H | 1% | S LPC | 0.01% | Clo. But | 0.1% | Clear | 8.94 | 63.0 |
| SMA 3000P* | 2.5% | 90H | 1% | S LPC | 0.01% | HC But | 0.1% | Clear | 8.86 | 33.1 |
| SMA 3000P* | 2.5% | 90H | 1% | S LPC | 0.01% | DEX A.A. | 0.25% | Clear | 8.84 | 10.52 |
| SMA 3000P* | 2.5% | 90H | 1% | S LPC | 0.01% | Cort. A. | 0.25% | Clear | 8.87 | 14.28 |
| SMA 3000P* | 2.5% | 90H | 1% | S LPC | 0.01% | HC A | 0.25% | Clear | 8.92 | 39.6 |
| SMA 3000P* | 2.5% | 90H | 1% | S LPC | 0.01% | Eusolex 2292 | 0.1 | Clear | 8.81 | 24.50 |
| SMA 3000P* | 2.5% | 90H | 1% | S LPC | 0.01% | Eusolex 4360 | 0.1 | Clear | 8.96 | 31.00 |
| SMA 3000P* | 2.5% | 90H | 1% | S LPC | 0.01% | Soy Iso. | 0.1 | Clear | 8.84 | 40.30 |
| SMA 3000P* | 2.5% | 90H | 1% | S LPC | 0.01% | Ros. Acid | 0.1 | Clear | 8.96 | 80.8 |
| SMA 3000P* | 2.5% | 90H | 1% | S LPC | 0.01% | Licorice CG | 0.1 | Clear | 8.78 | 60.9 |
| SMA 3000P* | 2.5% | 90H | 1% | S LPC | 0.01% | Green Tea Extract | 0.1 | Clear | 8.84 | 74.5 |
| SMA 3000P* | 2.5% | 90H | 1% | S LPC | 0.01% | Minoxidil | 0.1 | Clear | 8.91 | 10.86 |
| SMA 3000P* | 2.5% | 90H | 1% | S LPC | 0.01% | Erythro. | 0.1 | Clear | 8.86 | 18.20 |
| SMA 3000P* | 2.5% | 90H | 1% | S LPC | 0.01% | Neo. Sulphate | 0.1 | Clear | 8.82 | 42.80 |
| SMA 3000P* | 2.5% | 90H | 1% | S LPC | 0.01% | Keta. | 0.1 | Clear | 8.63 | 40.75 |
| SMA 3000P* | 2.5% | 90H | 1% | S LPC | 0.01% | Keta. | 0.4 | Clear | 8.83 | 74.5 |
| SMA 3000P* | 2.5% | 90H | 1% | S LPC | 0.01% | PABA | 0.1 | Clear | 8.89 | 23.20 |
| SMA 3000P* | 2.5% | 90H | 1% | S LPC | 0.01% | Boswellin CG | 0.1 | Clear | 8.93 | 64.50 |
| SMA 3000P* | 2.5% | 90H | 1% | S LPC | 0.01% | Chol Sulphate | 0.1 | Clear | 8.81 | 17.81 |
| SMA 3000P* | 2.5% | 90H | 1% | S LPC | 0.01% | 7-DHC | 0.1 | Clear | 8.91 | 7.28 |
| SMA 3000P* | 2.5% | 90H | 1% | S LPC | 0.01% | Melal. | 0.1 | Clear | 8.78 | 12.74 |
| SMA 3000P* | 2.5% | 90H | 1% | S LPC | 0.01% | Galanga | 0.1 | Clear | 8.94 | 9.34 |
| SMA 3000P* | 2.5% | 90H | 1% | S LPC | 0.01% | Cosm. | 0.1 | Clear | 8.88 | 63.7 |
| SMA 3000P* | 2.5% | 90H | 1% | S LPC | 0.01% | P-U | 0.1 | Clear | 8.75 | 15.2 |
| SMA 3000P* | 2.5% | 90H | 1% | S LPC | 0.01% | PT-40 | 0.25 | Clear | 8.99 | 23.45 |
| SMA 3000P* | 2.5% | 90H | 1% | S LPC | 0.01% | Cera. IIIB | 0.1 | Clear | 8.98 | 120.7 |
| SMA 3000P* | 2.5% | 90H | 1% | S LPC | 0.01% | Nystatin | 0.1 | Clear | 8.85 | 6.93 |
| SMA 3000P* | 2.5% | 90H | 1% | S LPC | 0.01% | Unisol S-22 | 0.15 | Clear | 8.94 | 9.46 |
| SMA 3000P* | 2.5% | 90H | 1% | S LPC | 0.01% | Avobenzene | 0.1 | Clear | 8.88 | 62.0 |
| SMA 3000P* | 2.5% | 90H | 1% | S LPC | 0.01% | Clot. | 0.1 | Clear | 8.78 | 5.91 |
| SMA 3000P* | 2.5% | 90H | 1% | S LPC | 0.01% | Cera HO3 | 0.1 | Clear | 8.68 | 6.14 |
| SMA 3000P* | 2.5% | 90H | 1% | S LPC | 0.01% | Questice | 0.25 | Clear | 8.84 | 28.9 |
| SMA 3000P* | 2.5% | 90H | 1% | S LPC | 0.01% | Unisex Bouquet | 0.1 | Clear | 8.88 | 214 |
| SMA 3000P* | 2.5% | 90H | 1% | S LPC | 0.01% | Apricosal | 0.25 | Clear | 8.78 | 16.12 |
| SMA 3000P* | 2.5% | 90H | 1% | S LPC | 0.01% | Fougere | 0.25 | Clear | 8.67 | 7.04 |
| SMA 3000P* | 2.5% | 90H | 1% | S LPC | 0.01% | Pep-mint Oil | 0.25 | Clear | 8.84 | 17.29 |
| SMA 3000P* | 2.5% | 90H | 1% | S LPC | 0.01% | NDGA | 0.1 | Clear | 8.98 | 27.7 |
| SMA 3000P* | 2.5% | 90H | 1% | S LPC | 0.01% | Vitamin $D_3$ | 0.25 | Clear | 8.59 | 19.78 |
| SMA 3000P* | 2.5% | 90H | 1% | S LPC | 0.01% | Caffeine | 0.25 | Clear | 8.84 | 14.69 |
| SMA 3000P* | 2.5% | 90H | 1% | S LPC | 0.01% | Herbalia Nettle | 0.20 | Clear | 8.85 | 54.2 |
| SMA 3000P* | 2.5% | 90H | 1% | S LPC | 0.01% | Horse Chestnut | 0.20 | Clear | 8.82 | 50.9 |
| SMA 3000P* | 2.5% | 90H | 1% | S LPC | 0.01% | Ginkgo | 0.20 | Clear | 8.92 | 12.89 |
| SMA 3000P* | 2.5% | 90H | 1% | S LPC | 0.01% | GSF | 0.20 | Clear | 8.95 | 28.8 |
| SMA 3000P* | 2.5% | 90H | 1% | S LPC | 0.01% | G38 | 0.20 | Clear | 8.79 | 27.7 |
| SMA 3000P* | 2.5% | 90H | 1% | SL 30-3 (S LPC content) | 0.05% (0.01%) | Octopirox | 0.80 | Clear | — | 3.52 |

— indicates not tested

*indicates the polymer was hydrolysed before use

† sample used for reconstitution test of freeze-dried material

Example 6

A Preparation Containing a Collagen Stimulating Agent

To exemplify the use of polymer/lipid macromolecular assemblies of the present invention in a cosmetic preparation, a composition of the invention was used to solubilise the collagen stimulating agent TECA, and combined with a preservative and viscosity modifiers.

Method

A stock emulsion of cosurfactant, membrane forming lipid and active was prepared at double the desired final concentration. Cosurfactant was dissolved in water while heating (approximately 50° C.) and stirring. Lipid was then added, followed by continued stirring and heating until a uniform emulsion is formed. The emulsion was then homogenised for 10 minutes. After re-heating to approximately 50° C. the active component was added slowly under stirring until a uniform emulsion was present. The final emulsion was then homogenised for a further 10 minutes.

A stock solution of each polymer was prepared at double (i.e. 5%) the desired final concentration of 2.5%. The polymer, which was supplied as styrene/maleic anhydride, was first hydrolysed by refluxing in water for two hours in the presence of excess sodium hydroxide, before being left at 4° C. for 48 hours to ensure that the reaction was complete. Stock solutions were prepared by mixing of the hydrolysed polymer with the appropriate volume of water.

Polymer/lipid mixtures were then prepared by the dropwise addition of the lipid containing emulsion to an equal volume of polymer solution while stirring and heating to approximately 50° C.

Preservative was then added to the solution and the pH adjusted. The resulting solution is referred to as Solution A and its composition is summarised in Table 13.

TABLE 13

| Solution A Composition | |
|---|---|
| Component | Concentration % |
| SMA3000P* | 2.5 |
| 90H | 1.0 |
| S-LPC | 0.01 |
| TECA | 0.8 |
| Phenonip | 0.1 |

*indicates the polymer was hydrolysed before use

Xanthan gum and carbopol were mixed with water and stirred until a uniform gel was formed. The pH was then adjusted to 7. The resulting solution is referred to as Solution B and its composition is summarised in Table 14.

TABLE 14

| Solution B Composition | |
|---|---|
| Component | Concentration % |
| Keldent ® | 1.5 |
| 980NF | 0.5 |

Solution A and Solution B were then mixed in equal volumes to produce the final preparation.

Polymers

SMA3000P was as described in Example 1.

Lipid 90H was as described in Comparative Example 1.

Surfactants

S LPC were as described in Comparative Example 1.

Active Agent

TECA was as described in Comparative Example 2.

Preservative

Phenonip is available from Clariant UK Ltd and is a blend of 2-phenoxyethanol and other agents (methylparaben, ethylparaben, propylparaben, butylparaben and isobutylparaben). It was utilised as a liquid at 60-80% purity.

Viscosity Modifiers

Keldent® is a xanthan gum, available from CP Kelco (UK) in the form of powder. CAS Ref 11138-66-2.

Carbopol® 980NF is a polymer of acrylic acid which is cross-linked with allylsucrose and is available from Noveon Inc/Surfachem Group Ltd (UK) in the form of a powder.

Results

A cosmetic preparation of the active agent TECA, which has poor water solubility, was successfully prepared in a clear and colourless aqueous gel at pH 7.

Example 7

A Cosmetic Preparation of an Anti-Oxidant

To exemplify the use of polymer/lipid macromolecular assemblies of the present invention in a cosmetic preparation, a composition of the invention was used to solubilise the anti-oxidant vitamin C derivative Asc-P, and combined with a preservative and viscosity modifiers.

Method

A stock emulsion of cosurfactant, membrane forming lipid and active was prepared at double the desired final concentration. Cosurfactant was dissolved in water while heating (approximately 50° C.) and stirring. Lipid was then added, followed by continued stirring and heating until a uniform emulsion is formed. The emulsion was then homogenised for 10 minutes. After re-heating to approximately 50° C. the active component was added slowly under stirring until a uniform emulsion was present. The final emulsion was then homogenised for a further 10 minutes.

A stock solution of each polymer was prepared at double (i.e. 5%) the desired final concentration of 2.5%. The polymer, which was supplied as styrene/maleic anhydride, was first hydrolysed by refluxing in water for two hours in the presence of excess sodium hydroxide, before being left at 4° C. for 48 hours to ensure that the reaction was complete. Stock solutions were prepared by mixing of the hydrolysed polymer with the appropriate volume of water.

Polymer/lipid mixtures were then prepared by the dropwise addition of the lipid containing emulsion to an equal volume of polymer solution while stirring and heating to approximately 50° C.

Preservative was then added to the solution and the pH adjusted. The resulting solution is referred to as Solution A and its composition is summarised in Table 15.

TABLE 15

| Solution A Composition | |
|---|---|
| Component | Concentration % |
| SMA3000P* | 2.5 |
| 90H | 1.0 |
| S-LPC | 0.01 |
| Asc-P | 0.1 |
| Phenonip | 0.1 |

*indicates the polymer was hydrolysed before use

Xanthan gum and carbopol were mixed with water and stirred until a uniform gel was formed. The pH was then adjusted to 7. The resulting solution is referred to as Solution B and its composition is summarised in Table 16.

TABLE 16

Solution B Composition

| Component | Concentration % |
|---|---|
| Keldent ® | 1.5 |
| 980NF | 0.5 |

Solution A and Solution B were then mixed in equal volumes to produce the final preparation.
Polymers
  SMA3000P was as described in Example 1.
Lipid
  90H was as described in Comparative Example 1.
Surfactants
  S LPC were as described in Comparative Example 1.
Active Agent
  Asc-P was as described in Example 5.
Preservative
  Phenonip was as described in Example 6.
Viscosity Modifiers
  Keldent® and Carbopol 980NF were as described in Example 6.
Results
  A cosmetic preparation of the active agent Asc-P, which has poor water solubility, was successfully prepared in a clear and colourless aqueous gel at pH 7.

Example 8

Incorporation of PagP into Compositions of the Invention for Structural Analysis Precipitated PagP (expressed and purified as a precipitate according to the previously published protocol by Hwang, P. M. et al. *Proc. Natl. Acad. Sci. USA* 2002 99(21):13560-13565) was dissolved in 5% SDS to give a final concentration of 0.5 mM and dialysed (molecular mass cutoff of 3500 Da) for 5 days against 50 mM sodium phosphate (pH 6) to remove SDS. β-octylglucopyranoside (β-OG) was slowly added to give a final concentration of 100 mM and then ethanol was added to 1%. The sample (ca. 3 ml at approximately 0.5 mM PagP) was added to a 10 ml solution of 2% DMPC (w/w) in 50 mM Tris.HCl (pH 8), 200 mM NaCl and 100 mM β-OG. β-OG was removed over the course of two hours using Biobeads (Bio-Rad) to yield an opaque solution. Subsequently, 10 ml of polymer solution (hydrolysed SMA3000P, as described in Example 1) at a concentration of 5% by weight was added in a 1:1 ratio (v/v) and left at room temperature for 5 minutes to allow formation of macromolecular assemblies. The solution was filtered (0.22 um) then purified using standard nickel affinity chromatography procedures. Column fractions were assessed for purity by using SDS/PAGE. The purest fractions were pooled and then purified further by size exclusion chromatography.
  Analysis of protein conformation was performed using Far UV circular dichroism (Far UV CD) and Fourier-Transform Infra-Red (FTIR) spectroscopy.

Example 9

Incorporation of Bacteriorhodopsin into Compositions of the Invention for Structural Analysis Lyophilised bacteriorhodopsin purple membrane from *Halobacterium halobium* (8 mg, Sigma Ltd.) was suspended in 1 ml of 50 mM Tris.HCl (pH 8.0), 200 mM NaCl and 2% DMPC (w/w), then incorporated into membrane by probe sonication. Polymer (hydrolysed SMA3000P, as described in Example 1) at a concentration of 5% by weight was added in a 1:1 ratio (v/v) and left at room temperature for 5 minutes to allow formation of macromolecular assemblies. The solution was filtered (0.22 um) then purified further by size exclusion chromatography.
  Analysis of conformation was performed using Far UV CD, visible CD and FTIR.

Example 10

Incorporation of Gramicidin into Compositions of the Invention for Structural Analysis Lyophilised gramicidin A from *Bacillus Brevis* (Sigma Ltd.) was solubilised in 100% ethanol to a final concentration of 20 mg/ml. The solution (80 ul) was then added slowly to a 3.5% by weight solution of DMPC/polymer macromolecular assemblies (1:2.5 lipid:hydrolysed SMA3000P ratio) in 50 mM Tris.HCl (pH 8) and 200 mM NaCl (920 ul). The sample was heated at 65° C. for 10 minutes then centrifuged (16000× g) to remove unincorporated material and finally purified using size exclusion chromatography.
  Analysis of conformation was performed by Far UV CD.

Example 11

Proposed Method for Determining Skin Absorption of Macromolecular Assemblies into the Skin (a) Using a Marker Agent
  Macromolecular assemblies of the invention which also incorporate a marker agent would be prepared by analogy to the compositions described previously. The marker agent could be a dye which is visible under normal light (e.g. D & C Red No. 27, also known as 2',4',5',7'-tetrabromo-4,5,6,7-tetrachlorofluorescein), or a fluorescent marker visible under UV light, either of which would have poor solubility in aqueous media absent the macromolecular assemblies of the invention. Other markers are possible, such as radio-labelled agents, but may be less desirable.
  An aqueous preparation of the macromolecular assemblies containing the marker is applied to a skin sample and a period of time allowed for absorption to occur. Excess aqueous preparation is then removed from skin surface prior to analysis of the extent of absorption. The extent of absorption is then measured using means appropriate for the marker in question. For example, markers visible under normal light may be quantified using commercially available detectors for a wavelength characteristic of the marker, or by photographing the absorption area and analysing the photograph using conventional image analysis means.
  Absorption depth can be investigated by using skin stripping techniques to remove layers of skin and by analysing the extent of absorption at each layer.

(b) By Measurement of Physiological Response Locally or Systemically

Macromolecular assemblies of the invention which also incorporate an active agent having poor water solubility are prepared by analogy to the compositions described previously. The agent will be one which leads to a physiological response which is detectable and quantifiable (e.g. vasodilators tend to increase skin redness locally and can systemically affect blood pressure, steroids can cause local vasoconstriction which leads to blanching).

An aqueous preparation of the macromolecular assemblies containing the active agent is applied to a skin sample and a period of time allowed for absorption to occur. Excess aqueous preparation is then removed from skin surface prior to analysis of the effects of absorption. The effects of absorption are then measured using means appropriate for the agent in question. For example, skin reddening/blanching may be quantified using commercially available detectors, or by photographing the absorption area and analysing the photograph using conventional image analysis means, systemic effects such as changes in blood pressure or concentration of active agent in the blood can be measured by conventional means known to those skilled in the art.

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The claims of this application may be directed to any feature or combination of features described herein. They may take the form of product, composition, process, or use claims and may include, by way of example and without limitation, the following claims:

The invention claimed is:

1. A composition comprising a lipid and copolymer of styrene and maleic acid, wherein the ratio of styrene to maleic acid monomer units is greater than 1.2:1 on a weight basis, and wherein the polymer and lipid are in the form of macromolecular assemblies of less than 100 nm in diameter.

2. A composition according to claim 1 wherein the ratio of styrene to maleic acid monomer units is greater than 2.5:1.

3. A composition according to claim 1, wherein the ratio of styrene to maleic acid monomer units is less than 4.5:1.

4. A composition according to claim 3, wherein the ratio of styrene to maleic acid monomer units is less than 3.5:1.

5. A composition according to claim 1, wherein the copolymer of styrene and maleic acid has an average molecular weight of less than 500,000 daltons.

6. A composition according to claim 5, wherein the copolymer of styrene and maleic acid has an average molecular weight of less than 20,000 daltons.

7. A composition according to claim 1, wherein the copolymer of styrene and maleic acid has an average molecular weight in the range 4,500 to 12,000 and a ratio of styrene to maleic acid of about 2:1, 3:1, or 4:1.

8. A composition according to claim 1, wherein the polymer and lipid macromolecular assemblies are stable in aqueous solution at a pH between 5.0-7.5.

9. A composition according to claim 8, wherein the polymer and lipid macromolecular assemblies are stable in aqueous solution at a pH between 6.5-7.5.

10. A composition according to claim 1, wherein the polymer and lipid macromolecular assemblies are stable in aqueous solution at a pH between 7.1-7.8.

11. A composition according to claim 1, wherein the lipid is a single component.

12. A composition according to claim 11, wherein the single component is a phosphatidyl choline.

13. A composition according to claim 11, wherein the single pure component is a phosphatidyl glycerol.

14. A composition according to claim 1, wherein the lipid is a mixture of components.

15. A composition according to claim 14, wherein the lipid is a lipid mixture of at least 50% phospholipids having a single headgroup type by weight.

16. A composition according to claim 14, wherein the lipid is a lipid mixture of at least 75% phospholipids having a single headgroup type by weight.

17. A composition according to claim 15, wherein the single headgroup type is a phosphatidyl choline.

18. A composition according to claim 1, wherein the lipid is derived from egg.

19. A composition according to claim 1, wherein the lipid is derived from soy.

20. A composition according to claim 1, wherein the ratio of copolymer to lipid is greater than 1:1 on a weight basis.

21. A composition according to claim 1, which further comprises a cosurfactant.

22. A composition according to claim 21, which cosurfactant is added in an amount equivalent to 0.1 to 5% of the weight of lipid in the composition.

23. A composition according to claim 22, which cosurfactant is added in an amount equivalent to 0.75 to 1.5% of the weight of lipid in the composition.

24. A composition according to claim 21, wherein the cosurfactant is a block copolymer of propylene oxide/ethylene oxide.

25. A composition according to claim 21, wherein the cosurfactant is lyso-phosphatidyl choline.

26. A composition according to claim 1, wherein the macromolecular assemblies are less than 50 nm in diameter.

27. A composition according to claim 1, which is in freeze-dried form.

28. An aqueous solution comprising a composition according to claim 1.

29. An aqueous solution according to claim 28, comprising 0.001-10% by weight of a composition according to claim 1.

30. An aqueous solution according to claim 28, comprising 10-20% by weight of a composition according to claim 1.

31. An aqueous solution according to claim 28, comprising greater than 20% by weight of a composition according to claim 1.

32. An aqueous solution according to claim 28, which is clear and stable and has a pH between 5.0-7.5.

33. An aqueous solution according to claim 28, which is clear and stable and has a pH between 6.5-7.5.

34. An aqueous solution according to claim 28, which is clear and stable and has a pH between 7.1-7.8.

35. A formulation comprising a composition according to claim 1 or an aqueous solution according to claim 28, which further comprises an active agent.

36. A formulation according to claim 35, wherein the active agent is an oil soluble vitamin or oil soluble vitamin derivative.

37. A formulation according to claim 35, wherein the active agent has a triterpenoid or steroidal nucleus.

38. A formulation according to claim 35, wherein the active agent is an oil soluble peptide.

39. A formulation comprising a composition according to claim 1 or an aqueous solution according to claim 28, which further comprises a membrane peptide or protein.

40. A cosmetic preparation comprising a formulation according to claim 35, which further comprises a cosmetically acceptable carrier or excipient.

41. A pharmaceutical preparation comprising a formulation according to claim 35, which further comprises a pharmaceutically acceptable carrier or excipient.

42. A method for the production of a composition according to claim 1 comprising:
(i) Preparing an aqueous solution of a non-alternating copolymer of styrene and maleic acid, wherein the ratio of styrene to maleic acid monomer units is greater than 1:1;
(ii) Preparing an aqueous lipid emulsion;
(iii) Mixing the lipid emulsion and aqueous solution of copolymer;
(iv) optionally adjusting the pH of the mixture where required to form the polymer/lipid macromolecular assemblies;
(v) Optionally removing the water.

43. A method for the production of a formulation according to claim 35 comprising:
(i) Preparing an aqueous solution of a non-alternating copolymer of styrene and maleic acid, wherein the ratio of styrene to maleic acid monomer units is greater than 1:1;
(ii) Preparing an aqueous emulsion of lipid and active agent;
(iii) Mixing the aqueous emulsion and aqueous solution of copolymer;
(iv) Optionally adjusting the pH of the mixture where required to form the polymer/lipid macromolecular assemblies;
(v) Optionally removing the water.

44. A method of solubilizing a lipid in aqueous solution comprising forming macromolecular assemblies of the lipid and a non-alternating copolymer of styrene and maleic acid of less than 100 nm in diameter, wherein the ratio of styrene to maleic acid monomer units is greater than 1:1 on a weight basis.

45. A method of solubilizing an active agent having poor aqueous solubility in aqueous solution comprising forming macromolecular assemblies of the lipid, active agent, and a non-alternating copolymer of styrene and maleic acid of less than 100 nm in diameter, wherein the ratio of styrene to maleic acid monomer units is greater than 1:1 on a weight basis.

* * * * *

UNITED STATES PATENT AND TRADEMARK OFFICE
CERTIFICATE OF CORRECTION

PATENT NO. : 8,623,414 B2  
APPLICATION NO. : 11/921262  
DATED : January 7, 2014  
INVENTOR(S) : Stephen Tonge It is certified that error appears in the above-identified patent and that said Letters Patent is hereby corrected as shown below:

Title page, item (73) Assignee should read as follows:

(73) Assignee: Malvern Cosmeceutics Limited,
Worchestershire (GB)

Signed and Sealed this
First Day of April, 2014

Michelle K. Lee
*Deputy Director of the United States Patent and Trademark Office*